(12) United States Patent  
Marnfeldt et al.

(10) Patent No.: US 8,364,280 B2  
(45) Date of Patent: Jan. 29, 2013

(54) ENGAGEMENT TOOL FOR IMPLANTABLE MEDICAL DEVICES

(75) Inventors: Goran N. Marnfeldt, Hollviken (SE); Rafael Carbunaru, Valley Village, CA (US); Kelly H. McClure, Simi Valley, CA (US); Matthew I. Haller, Valley Village, CA (US); Tom Xiaohai He, Simi Valley, CA (US); Todd K. Whitehurst, Valencia, CA (US); Meredith L. Anderson, Newhall, CA (US); James C. Makous, Santa Clarita, CA (US); Kristen N. Jaax, Santa Clara, CA (US); Peter K. Johnson, Newhall, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 601 days.

(21) Appl. No.: 12/506,890

(22) Filed: Jul. 21, 2009

(65) Prior Publication Data

US 2009/0281605 A1 Nov. 12, 2009

Related U.S. Application Data

(62) Division of application No. 11/136,938, filed on May 24, 2005, now abandoned.

(60) Provisional application No. 60/575,616, filed on May 28, 2004.

(51) Int. Cl.
*A61N 1/00* (2006.01)
(52) U.S. Cl. ....................................................... 607/116
(58) Field of Classification Search .................. 607/116; 606/108
See application file for complete search history.

(56) References Cited

U.S. PATENT DOCUMENTS

| | | |
|---|---|---|
| 3,352,306 A | 11/1967 | Hirsch |
| 3,760,984 A | 9/1973 | Theeuwes |
| 3,845,770 A | 11/1974 | Theeuwes et al. |
| 3,884,220 A | 5/1975 | Hartnett |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,103,690 A | 8/1978 | Harris |
| 4,111,202 A | 9/1978 | Theeuwes |
| 4,111,203 A | 9/1978 | Theeuwes |
| 4,137,920 A | 2/1979 | Bonnet |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |

(Continued)

FOREIGN PATENT DOCUMENTS

| | | |
|---|---|---|
| GB | 2307861 | 11/1997 |
| WO | WO 97/18857 | 5/1997 |

(Continued)

*Primary Examiner* — Carl H Layno
*Assistant Examiner* — Paula J Stice
(74) *Attorney, Agent, or Firm* — Vista IP Law Group LLP

(57) ABSTRACT

Systems for adjusting a position of an implanted medical device within a patient include an engagement tool configured to couple to the implanted medical device. The engagement tool adjusts the position of the medical device when coupled to the implanted medical device. Methods of adjusting a position of an implanted medical device within a patient include locating the implanted medical device, coupling an engagement tool to the medical device, and adjusting a position of the engagement tool to adjust the position of the medical device.

27 Claims, 24 Drawing Sheets

U.S. PATENT DOCUMENTS

| | | | |
|---|---|---|---|
| 4,360,019 A | 11/1982 | Portner et al. | |
| 4,402,323 A | 9/1983 | White | |
| 4,471,777 A * | 9/1984 | McCorkle, Jr. | 606/129 |
| 4,487,603 A | 12/1984 | Harris | |
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,862,891 A | 9/1989 | Smith | |
| 4,865,845 A | 9/1989 | Eckenhoff et al. | |
| 4,874,377 A | 10/1989 | Newgard et al. | |
| 4,886,065 A | 12/1989 | Collins, Jr. | |
| 4,941,874 A | 7/1990 | Sandow et al. | |
| 4,994,028 A | 2/1991 | Leonard et al. | |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,098,407 A | 3/1992 | Okamura | |
| 5,112,614 A | 5/1992 | Magruder et al. | |
| 5,123,905 A | 6/1992 | Kelman | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,248,301 A | 9/1993 | Koenig, Jr. et al. | |
| 5,250,065 A | 10/1993 | Clement et al. | |
| 5,290,310 A | 3/1994 | Makower et al. | |
| 5,300,079 A | 4/1994 | Niezink et al. | |
| 5,312,439 A | 5/1994 | Loeb | |
| 5,324,306 A | 6/1994 | Makower et al. | |
| 5,392,791 A | 2/1995 | Nyman | |
| 5,405,367 A | 4/1995 | Schulman et al. | |
| 5,466,242 A | 11/1995 | Mori | |
| 5,501,703 A | 3/1996 | Holsheimer et al. | |
| 5,520,660 A | 5/1996 | Loos et al. | |
| 5,536,248 A | 7/1996 | Weaver et al. | |
| 5,571,136 A | 11/1996 | Weaver | |
| 5,639,276 A | 6/1997 | Weinstock et al. | |
| 5,728,396 A | 3/1998 | Peery et al. | |
| 5,775,331 A | 7/1998 | Raymond et al. | |
| 5,817,061 A | 10/1998 | Goodwin et al. | |
| 5,827,293 A | 10/1998 | Elliott | |
| 5,882,331 A | 3/1999 | Sasaki | |
| 5,938,688 A | 8/1999 | Schiff | |
| 5,984,890 A | 11/1999 | Gast et al. | |
| 5,987,352 A | 11/1999 | Klein et al. | |
| 5,993,204 A | 11/1999 | Stubbs | |
| 6,010,487 A | 1/2000 | DeMichele et al. | |
| 6,016,449 A | 1/2000 | Fischell et al. | |
| 6,027,509 A | 2/2000 | Schatz et al. | |
| 6,039,762 A | 3/2000 | McKay | |
| 6,051,017 A | 4/2000 | Loeb et al. | |
| 6,061,596 A | 5/2000 | Richmond et al. | |
| 6,096,038 A | 8/2000 | Michelson | |
| 6,120,508 A | 9/2000 | Grunig et al. | |
| 6,143,033 A | 11/2000 | Paul et al. | |
| 6,164,284 A | 12/2000 | Schulman et al. | |
| 6,174,311 B1 | 1/2001 | Branch et al. | |
| 6,175,764 B1 | 1/2001 | Loeb et al. | |
| 6,181,965 B1 | 1/2001 | Loeb et al. | |
| 6,183,469 B1 * | 2/2001 | Thapliyal et al. | 606/41 |
| 6,185,452 B1 | 2/2001 | Schulman et al. | |
| 6,185,455 B1 | 2/2001 | Loeb et al. | |
| 6,208,894 B1 | 3/2001 | Schulman et al. | |
| 6,214,032 B1 | 4/2001 | Loeb et al. | |
| 6,219,580 B1 | 4/2001 | Faltys et al. | |
| 6,235,001 B1 | 5/2001 | O'Holloran et al. | |
| 6,241,771 B1 | 6/2001 | Gresser et al. | |
| 6,259,953 B1 | 7/2001 | Lucchesi et al. | |
| 6,272,382 B1 | 8/2001 | Faltys et al. | |
| 6,277,094 B1 | 8/2001 | Schendel | |
| 6,277,149 B1 | 8/2001 | Boyle et al. | |
| 6,304,785 B1 | 10/2001 | McCreery et al. | |
| 6,306,125 B1 | 10/2001 | Parker et al. | |
| 6,308,101 B1 | 10/2001 | Faltys et al. | |
| 6,312,258 B1 | 11/2001 | Ashman | |
| 6,315,721 B2 | 11/2001 | Schulman et al. | |
| 6,350,274 B1 | 2/2002 | Li | |
| 6,368,315 B1 | 4/2002 | Gillis et al. | |
| 6,379,351 B1 | 4/2002 | Thapliyal et al. | |
| 6,381,496 B1 | 4/2002 | Meadows et al. | |
| 6,428,556 B1 | 8/2002 | Chin | |
| 6,482,179 B1 | 11/2002 | Chu et al. | |
| 6,487,446 B1 | 11/2002 | Hill et al. | |
| 6,516,227 B1 | 2/2003 | Meadows et al. | |
| 6,530,896 B1 | 3/2003 | Elliott | |
| 6,539,263 B1 | 3/2003 | Schiff et al. | |
| 6,553,263 B1 | 4/2003 | Meadows et al. | |
| 6,579,224 B1 | 6/2003 | Burton et al. | |
| 6,582,441 B1 | 6/2003 | He et al. | |
| 6,607,547 B1 | 8/2003 | Chin | |
| 6,620,151 B2 | 9/2003 | Blischak et al. | |
| 6,652,569 B1 | 11/2003 | Taylor et al. | |
| 6,666,845 B2 | 12/2003 | Hooper et al. | |
| 6,679,917 B2 | 1/2004 | Ek | |
| 6,706,052 B1 | 3/2004 | Chin | |
| 6,712,826 B2 | 3/2004 | Lui | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,802,846 B2 | 10/2004 | Hauschild et al. | |
| 7,169,172 B2 | 1/2007 | Levine et al. | |
| 7,351,244 B2 | 4/2008 | Hamada | |
| 8,005,536 B2 * | 8/2011 | Imran | 600/547 |
| 2002/0049394 A1 | 4/2002 | Roy et al. | |
| 2002/0188252 A1 | 12/2002 | Bardy | |
| 2002/0188311 A1 | 12/2002 | Ferrera et al. | |
| 2002/0188344 A1 | 12/2002 | Bolea et al. | |
| 2002/0193859 A1 | 12/2002 | Schulman et al. | |
| 2003/0065353 A1 | 4/2003 | Horzewski et al. | |
| 2003/0078618 A1 | 4/2003 | Fey et al. | |
| 2003/0114905 A1 | 6/2003 | Kuzma | |
| 2004/0010261 A1 | 1/2004 | Hoag et al. | |
| 2004/0010262 A1 | 1/2004 | Parkinson et al. | |
| 2004/0176797 A1 | 9/2004 | Opolski | |
| 2005/0113923 A1 | 5/2005 | Acker et al. | |
| 2006/0009740 A1 | 1/2006 | Higgins et al. | |
| 2008/0027554 A1 | 1/2008 | Talmadge | |

FOREIGN PATENT DOCUMENTS

| | | |
|---|---|---|
| WO | WO 00/01320 | 1/2000 |
| WO | WO 2005/118057 | 12/2005 |

* cited by examiner

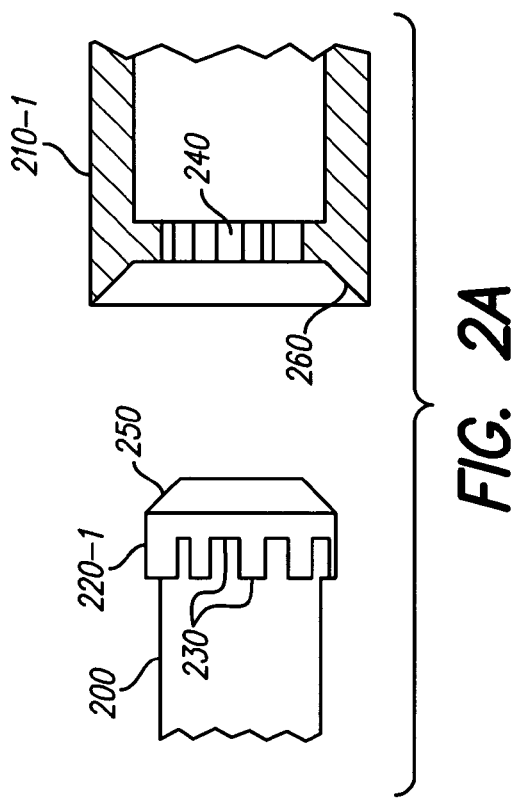
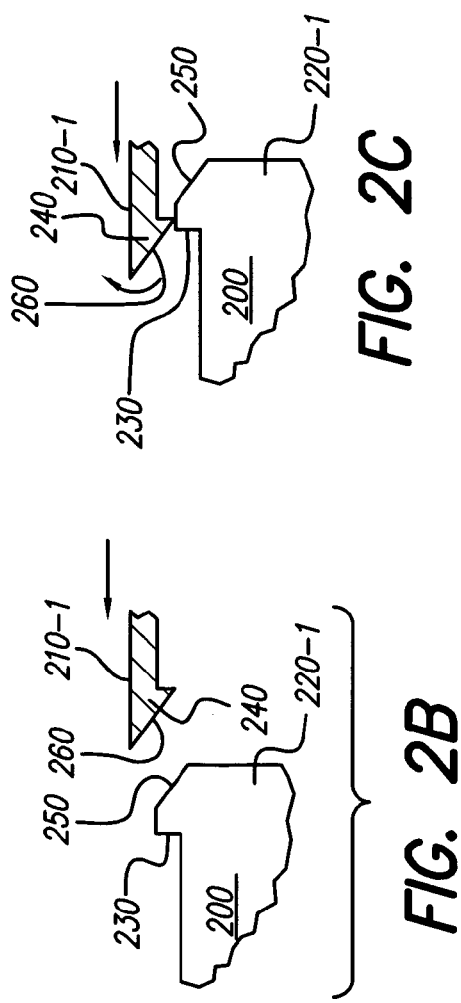
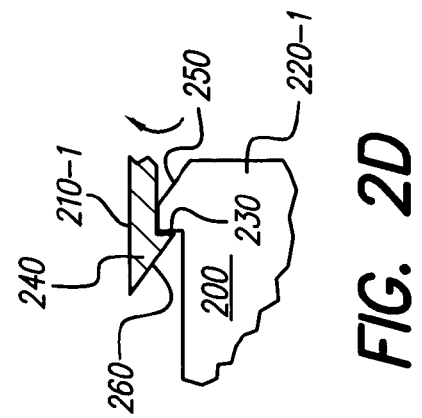
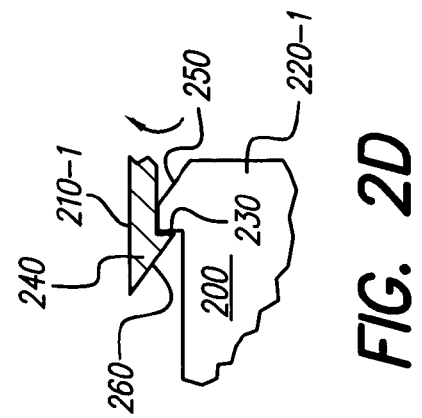

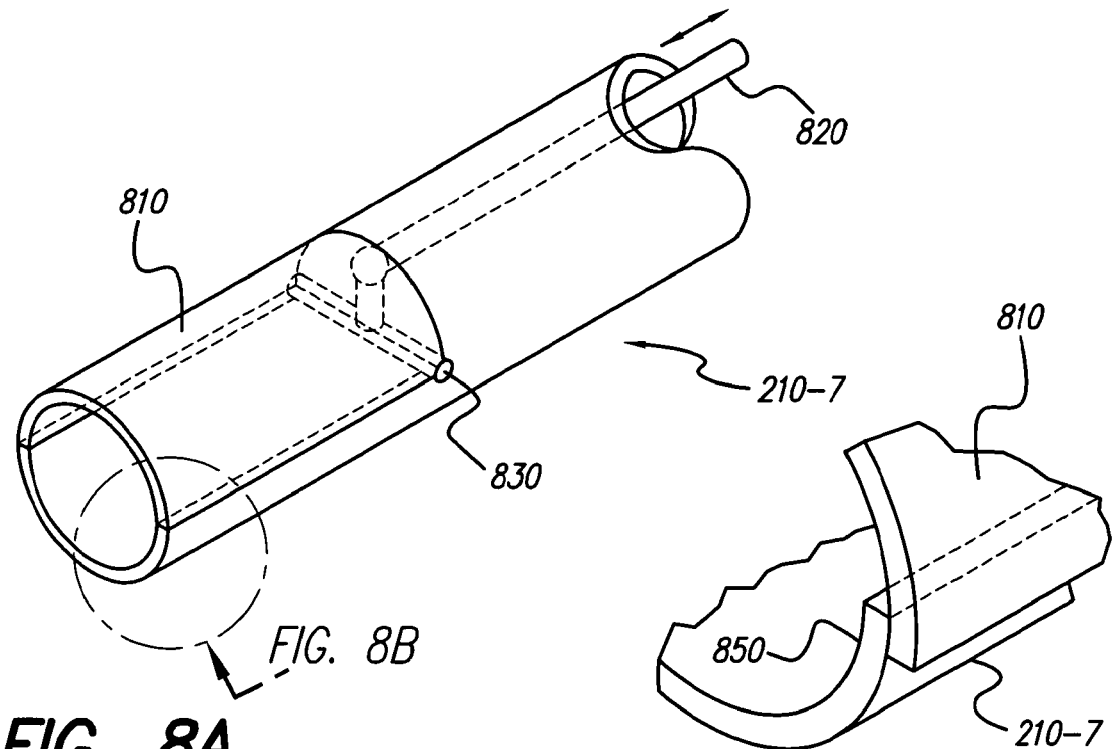
FIG. 8A
FIG. 8B
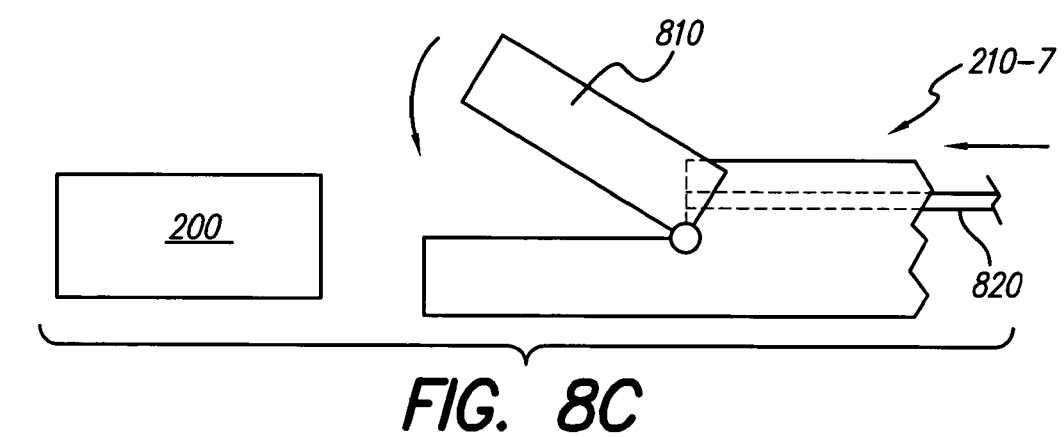
FIG. 8C
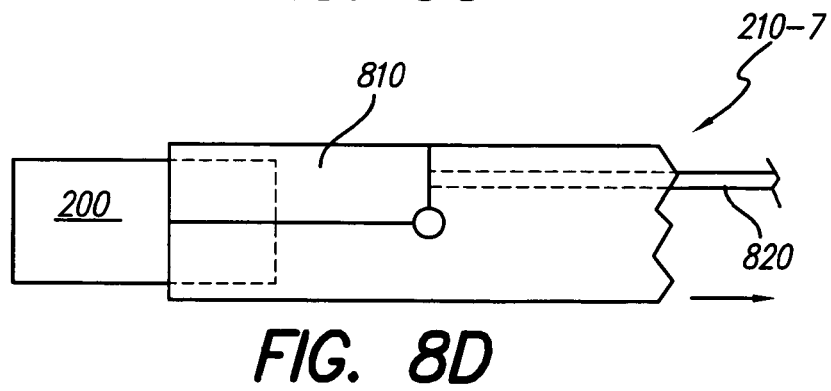
FIG. 8D

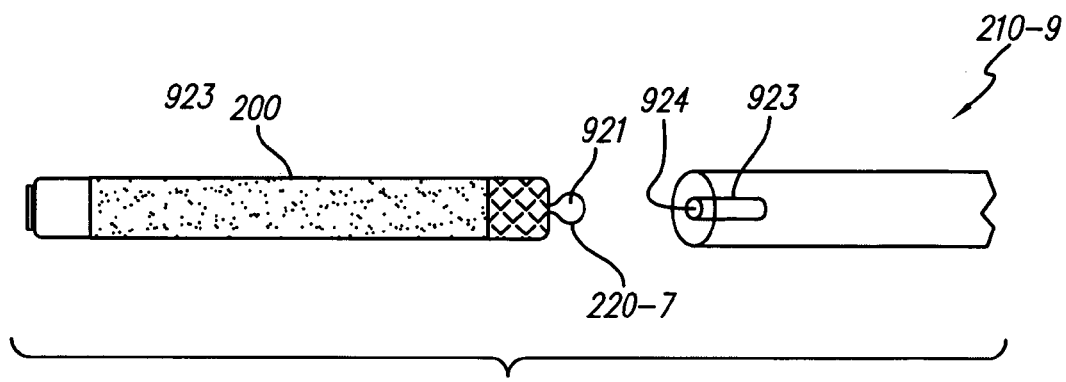
FIG. 12B
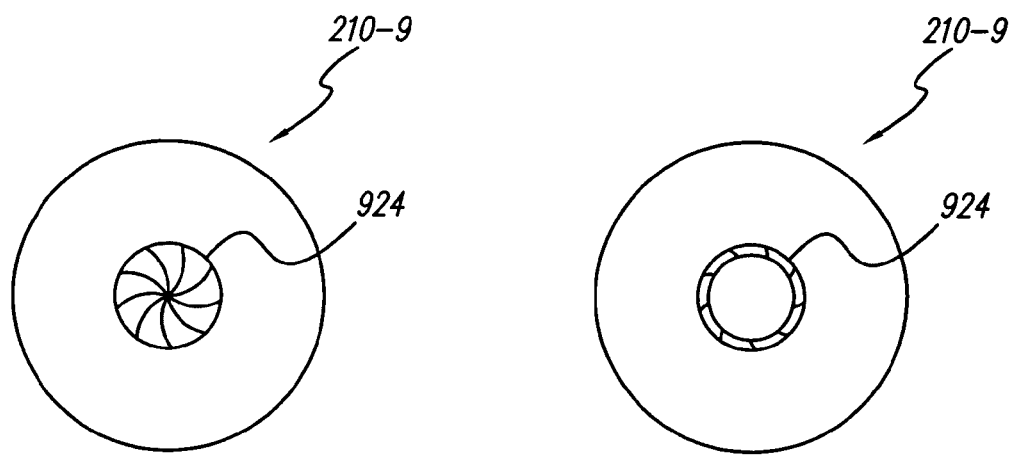
FIG. 12C   FIG. 12D

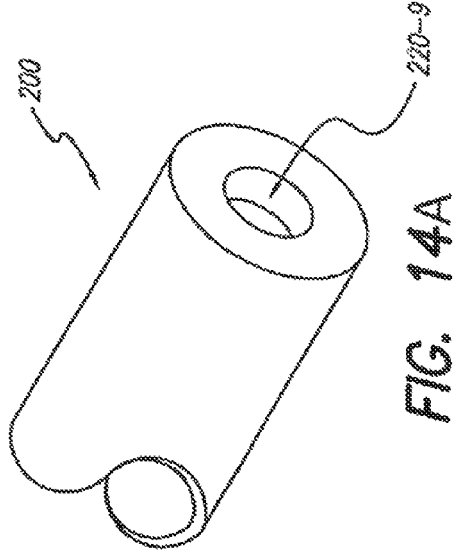
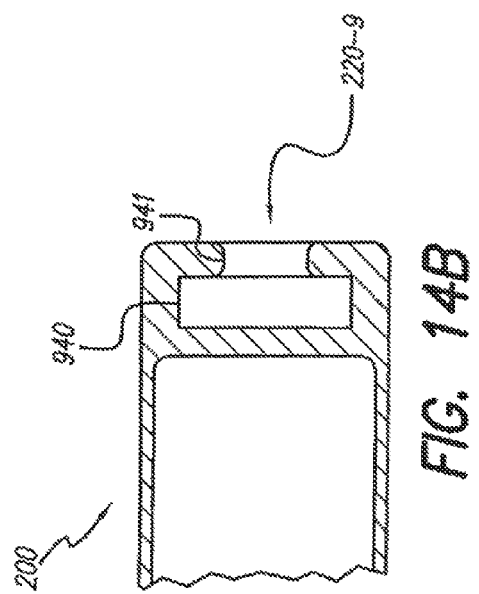

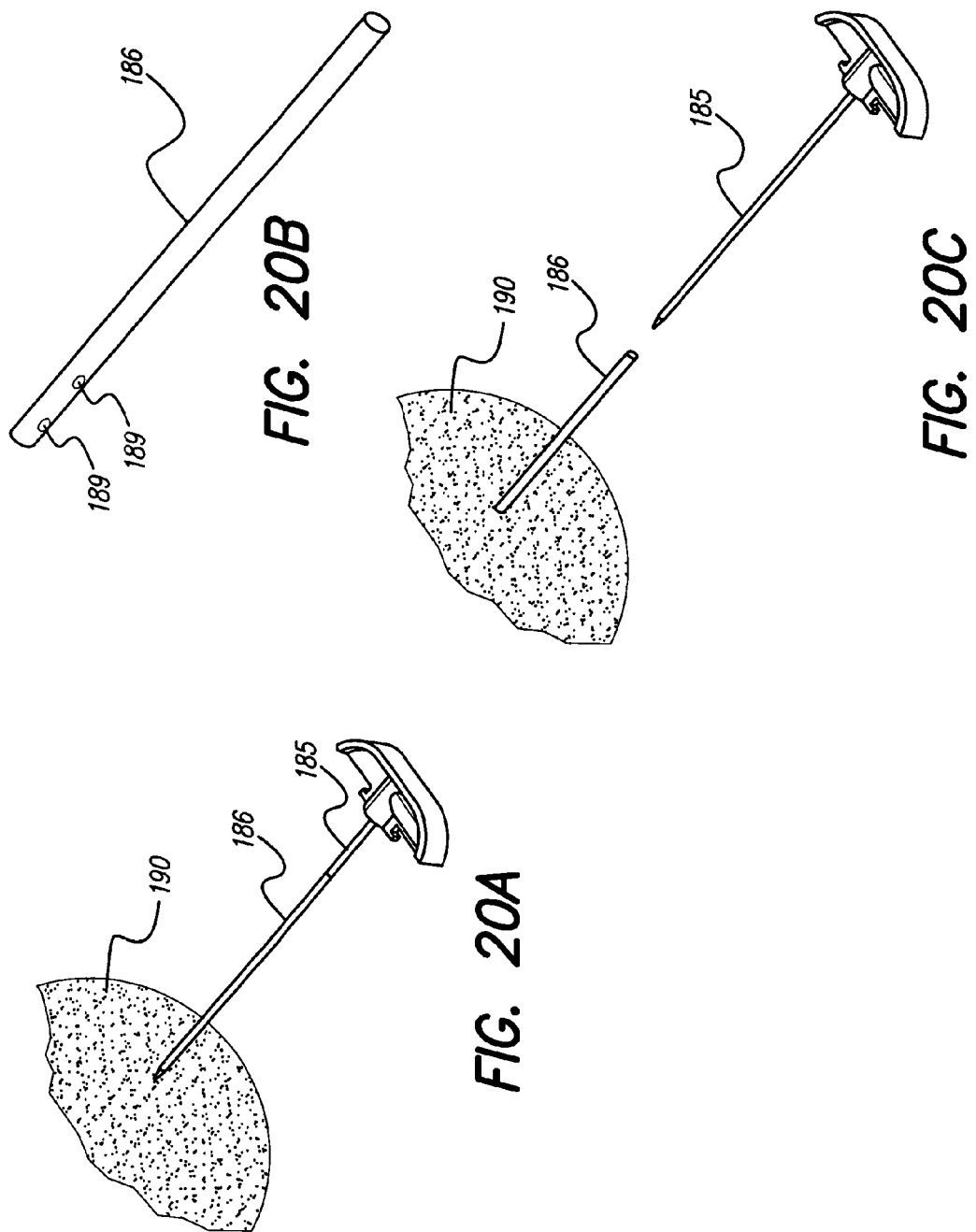

ENGAGEMENT TOOL FOR IMPLANTABLE MEDICAL DEVICES

RELATED APPLICATIONS

The present application is a divisional of U.S. patent application Ser. No. 11/136,938, filed May 24, 2005 now abandoned, which claims the benefit under 35 U.S.C. §119(e) of Provisional Application Ser. No. 60/575,616, filed May 28, 2004, which is incorporated hereby reference in its entirety.

BACKGROUND

A wide variety of medical conditions and disorders have been successfully treated using miniature implantable medical devices. For example, one type of implantable medical device is an implantable stimulator. Implantable stimulators stimulate internal tissue, such as nerves, by emitting an electrical stimulation current according to programmed stimulation parameters.

One class of implantable stimulators, also known as BION® devices (where BION® is a registered trademark of Advanced Bionics Corporation, of Valencia, Calif.), are typically characterized by a small, cylindrical housing containing electronic circuitry that produces an electric stimulation current between spaced electrodes. These stimulators, also referred to as microstimulators, are implanted proximate to the target tissue so that the stimulation current produced by the electrodes stimulates the target tissue to reduce symptoms or otherwise provide therapy for a wide variety of conditions and disorders.

For example, urinary urge incontinence may be treated by stimulating the nerve fibers proximal to the pudendal nerves of the pelvic floor. Erectile or other sexual dysfunctions may be treated by providing stimulation of the cavernous nerve(s). Other disorders, e.g., neurological disorders caused by injury or stroke, may be treated by providing stimulation to other appropriate nerve(s).

An example of an implantable device for tissue stimulation is described in U.S. Pat. No. 5,312,439, "Implantable Device Having an Electrolytic Storage Electrode." U.S. Pat. No. 5,312,439 is incorporated herein by reference in its entirety.

Another exemplary microstimulator is described in U.S. Pat. No. 5,193,539, "Implantable Microstimulator," which patent is also incorporated herein by reference in its entirety. This patent describes a microstimulator in which power and information for operating the microstimulator are received through a modulated, alternating magnetic field. This is accomplished with a coil in the microstimulator that is adapted to function as the secondary winding of a transformer. This induction coil receives energy from an external device outside the patient's body. A capacitor is then used to store the received electrical energy. This stored energy can then be used to generate a stimulation current through the microstimulator's exposed electrodes under the control of electronic control circuitry.

In U.S. Pat. Nos. 5,193,540 and 5,405,367, which patents are incorporated herein by reference in their respective entireties, a structure and method of manufacture for an implantable microstimulator are disclosed. The microstimulator has a structure which is manufactured to be substantially encapsulated within a hermetically-sealed housing that is inert to body fluids. The microstimulator structure is also of a size and shape capable of implantation in a living body with appropriate surgical tools. Within the microstimulator, an induction coil receives energy or data from outside the patient's body.

In yet another example, U.S. Pat. No. 6,185,452, which patent is likewise incorporated herein by reference in its entirety, discloses a device configured for implantation beneath a patient's skin for the purpose of nerve or muscle stimulation and/or parameter monitoring and/or data communication. Such a device contains a power source for powering the internal electronic circuitry. This power supply is a battery that may be externally charged each day. Similar battery specifications are found in U.S. Pat. No. 6,315,721, which patent is additionally incorporated herein by reference in its entirety.

In another example, such microstimulator systems prevent and/or treat various disorders associated with prolonged inactivity, confinement or immobilization of one or more muscles. Such microstimulators are taught, e.g., in U.S. Pat. Nos. 6,061,596 "Method for Conditioning Pelvis Musculature Using an Implanted Microstimulator;" U.S. Pat. No. 6,051,017 "Implantable Microstimulator and Systems Employing the Same;" U.S. Pat. No. 6,175,764 "Implantable Microstimulator System for Producing Repeatable Patterns of Electrical Stimulation; U.S. Pat. No. 6,181,965 "Implantable Microstimulator System for Prevention of Disorders;" U.S. Pat. No. 6,185,455 "Methods of Reducing the Incidence of Medical Complications Using Implantable Microstimulators;" and U.S. Pat. No. 6,214,032 "System for Implanting a Microstimulator." These patents are incorporated herein by reference in their respective entireties.

It is often desirable to remove or explant a medical device, such as a stimulator, that has been implanted within a patient. For example, an implanted medical device may be removed when the therapy provided by the device is not longer needed or desired. Additional reasons for removing a medical device from a patient include, but are not limited to, battery depletion, poor or unacceptable performance by the device, and device malfunction.

Likewise, it is often desirable to adjust the position an implanted medical device within the patient. For example, the position of an implanted medical device may be adjusted to optimize device performance, stimulate different tissue, or alleviate pain.

However, the depth and location within the patient often make it difficult to remove or adjust the position of many implanted medical devices. Furthermore, scar tissue often typically forms around, and attaches to, a medical device after it has been implanted. This scar tissue may further complicate the removal or repositioning of an implanted medical device. Thus, significant improvements related to the engagement, manipulation, movement, interconnection, implantation, and explantation of implantable medical devices are desirable.

SUMMARY

Systems for adjusting a position of an implanted medical device within a patient include an engagement tool configured to couple to the implanted medical device. The engagement tool adjusts the position of the medical device when coupled to the implanted medical device.

Methods of adjusting a position of an implanted medical device within a patient include locating the implanted medical device, coupling an engagement tool to the medical device, and adjusting a position of the engagement tool to adjust the position of the medical device.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 2A is a side view of the end of an implantable medical device and a cross-sectional view of a corresponding engagement tool according to principles described herein.

FIG. 2B is a cross-sectional close-up view of a tooth of the engagement tool of FIG. 2A prior to engaging with one of the edges of an engagement component of an implantable medical device according to principles described herein.

FIG. 2C is a cross-sectional close-up view of the tooth as it is engaging with the edge of the engagement component according to principles described herein.

FIG. 2D is a cross-sectional close-up view of the tooth after it has engaged with the edge of the engagement component according to principles described herein.

FIG. 8A is a perspective view of another exemplary engagement tool according to principles described herein.

FIG. 8B is a close-up view of a clamping member that is a part of the engagement tool of FIG. 8A according to principles described herein.

FIG. 8C is a side view of the engagement tool of FIG. 8A prior to engaging with an implantable medical device according to principles described herein.

FIG. 8D is a side view of the engagement tool of FIG. 8A fully engaged with the implanted medical device according to principles described herein.

FIG. 12B is a side view showing the engagement component of FIG. 12A and a corresponding engagement tool according to principles described herein.

FIGS. 12C and 12D show end views of the engagement tool of FIG. 12B according to principles described herein.

FIG. 14A is a perspective view of another exemplary engagement component according to principles described herein.

FIG. 14B is a cross-sectional view of the engagement component of FIG. 14A according to principles described herein.

FIGS. 20A-20G illustrate an exemplary method of gradually enlarging a channel that leads to the implanted medical device according to principles described herein.

Throughout the drawings, identical reference numbers designate similar, but not necessarily identical, elements.

DETAILED DESCRIPTION

Figure 1:
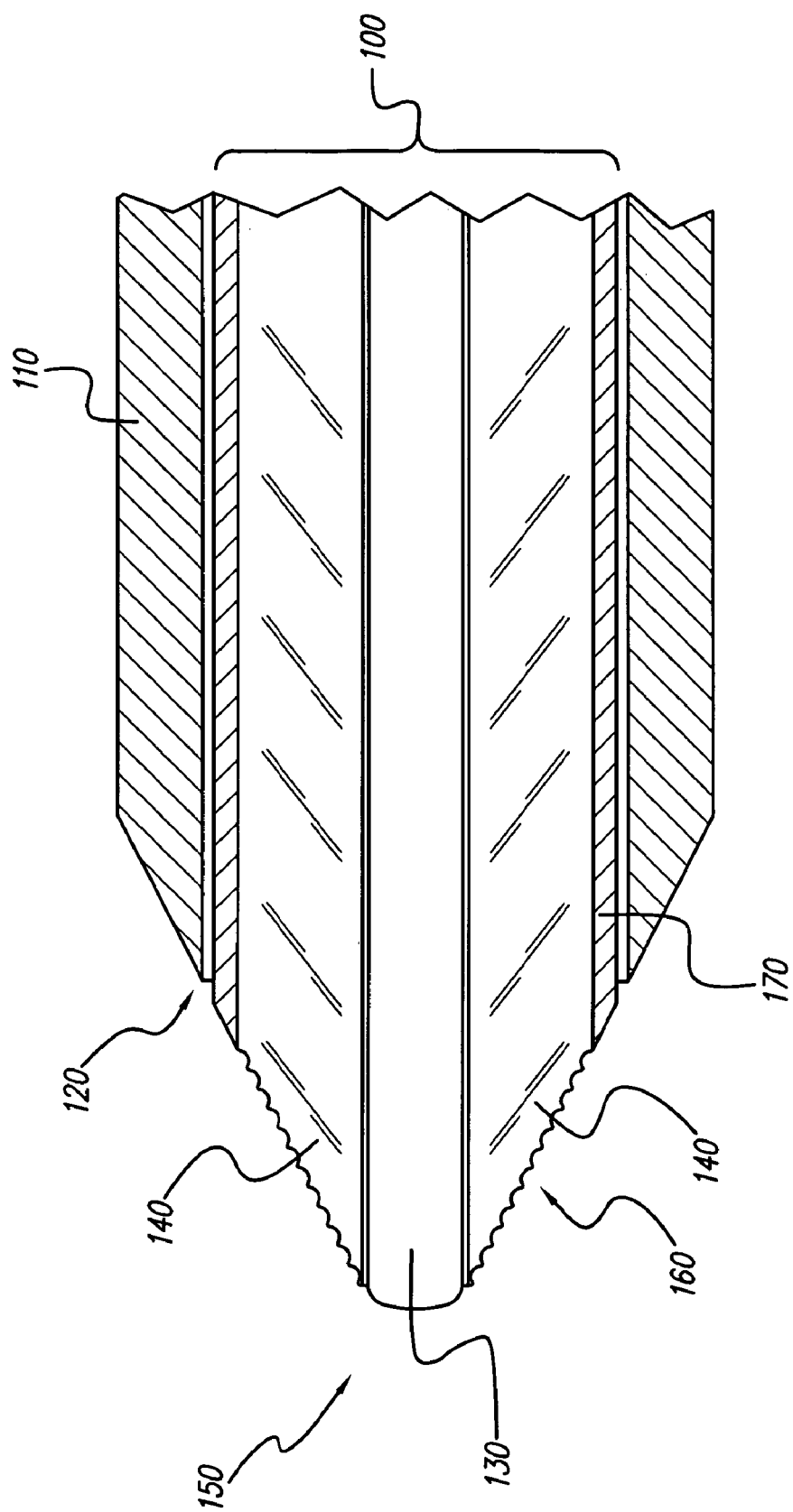
FIG. 1 is a cross-sectional view of a blunt optical needle within a cannula that may be used to locate an implanted medical device according to principles described herein.

A number of engagement tools, engagement components, systems, and methods for engaging, manipulating, moving, interconnecting, implanting, and/or explanting an implanted medical device are described herein. The various embodiments described herein, and equivalents thereof, may each include multiple elements, features, and benefits. Any of these elements, features, and/or benefits may be combined with any other elements, features, and/or benefits of any other embodiment described herein, and its equivalents.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

The terms "implantable medical device" and "implanted medical device" will be used interchangeably herein and in the appended claims to refer to any medical device or component that is pr cam be implanted within a patient and that may be engaged, manipulated, moved, interconnected, implanted, and/or explanted with the engagement tools and components described herein. The implantable medical device may include, but is not limited to, a stimulator, microstimulator, catheter, lead, electrode, stent, pacemaker, bone fixation device, pump, defibrillator, or any other device or component that is implanted within the patient.

A number of engagement tools and engagement components will be described in connection with FIGS. 1-23. An engagement tool is a tool or device configured to engage a medical device for purposes of manipulating, moving, repositioning, interconnecting, implanting, and/or explanting the medical device. As used herein and in the appended claims, the term "engagement tool" will be used to refer specifically to any of the engagement tools described in connection with FIGS. 1-23 or any equivalents thereof. An "engagement component" is a structure or device coupled to an implanted medical device that is configured to engage with an engagement tool for purposes of manipulating, moving, repositioning, interconnecting, implanting, and/or explanting the medical device. As used herein and in the appended claims, the term "engagement component" will be used to refer specifically to any of the engagement components described in connection with FIGS. 1-23 or any equivalents thereof.

The examples given herein in connection with FIGS. 1-23 describe various methods of using an engagement tool and/or an engagement component to explant or extract an implanted medical device and are for illustrative purposes only. It will be recognized that the engagement tools and components may additionally or alternatively be used to engage, manipulate, move, reposition, interconnect, and/or implant an implantable medical device.

Before removing or explanting an implanted medical device from a patient, it may be necessary for a surgeon to first locate the implanted medical device. FIG. 1 is a cross-sectional view of a blunt optical needle (100) within a cannula (110) that may be used to locate an implanted medical device. In some embodiments, the cannula (110) has an inner diameter slightly larger than that of the implanted medical device.

As shown in FIG. 1, the cannula (110) includes a cutting edge (120) at its proximal end. The cutting edge (120) is configured to cut through tissue, thus allowing the cannula (110) to be advanced into the body. As will be described in more detail below, the cutting edge (120) also serves to cut tissue away from the implanted medical device so that the medical device can be removed from the patient. As mentioned above, scar tissue tends to form around and attach to an implanted medical device over time.

The blunt optical needle (100) is configured to allow a surgeon to locate an implanted medical device. The needle (100) includes a blunt tip (150) that serves to spread tissue apart in a natural dissection pattern as the needle (100) advances through the tissue towards the implanted medical device. By spreading tissue rather than cutting through the fibers of tissue, the needle (100) will likely cause less damage along the pathway of the needle (100), thus decreasing the risk of complications during surgery, increasing the speed with which the pathway wound will heal, and decreasing the amount of subsequent scar tissue. However, it will be recognized that the tip of the needle (100) may alternatively be sharp or pointed as best serves a particular application.

In some embodiments, the needle (100) also includes a light guide (130) surrounded by a transparent light conductor (140) for illumination. A supportive material (170), such as a biocompatible metal, may form the outer surface of the needle (100), thus providing structural support to the light guide (130) and transparent light conductor (140).

The light guide (130) (also referred to as a visual port) may be constructed out of a glass optical fiber, for example, and may be connected at its distal end to a light source (not shown). Light is transmitted via the light guide (130) to the blunt tip (150) of the needle (100) and to the surrounding transparent light conductor (140).

A Fresnel lens pattern (160) included at a proximal end of the transparent light conductor (140) serves to diffract light to surrounding tissue. Thus, a surgeon using the blunt needle (100) to locate an implanted medical device may use the light emitted from the blunt tip (150) and from the Fresnel lens pattern (160) in conjunction with an endoscope or other visualization means (whether intrusive or not) to view the surrounding environment of the blunt tip (150).

After the cannula (110) and the needle (100) have arrived at or located the implanted medical device, the blunt needle (100) is removed from the lumen of the cannula (110). An engagement tool may then be inserted into the lumen of the cannula (110) and guided to the implanted medical device.

The engagement tool may then be used to explant or reposition the implanted medical device.

In some embodiments, a surgeon may also use the blunt tip (150) of the needle (100) to enlarge, expand, and/or unencumber one or more locations within the body of a patient by injecting air or any other suitable gas into the body through the needle (100).

A number of additional or alternative methods and systems for locating the implanted medical device may be used. For example, live or still images from fluoroscopy, x-ray, ultrasound, computerized axial tomography (CT), positron emission tomography (PET), magnetic resonance imaging (MRI), or any other imaging device may be used to locate the implanted medical device. Manual palpation may also be used to locate the implanted medical device. Any of these methods and systems for locating the implanted medical device may additionally or alternatively be used to assist the surgeon in the extraction or repositioning of the implanted medical device.

A number of engagement tools will be described below in connection with FIGS. 2-9. The examples given herein in connection with FIGS. 2-9 describe various methods of using an engagement tool to explant an implanted medical device for illustrative purposes only. It will be recognized that the engagement tools described in connection with FIGS. 2-9 may additionally or alternatively be used to engage, manipulate, move, interconnect, or implant an implantable medical device.

FIG. 2A is a side view of the end of an implantable medical device (200) and a cross-sectional view of a corresponding engagement tool (210-1). As shown in FIG. 2A, an engagement component (220-1) is coupled to the medical device (200). Although a single engagement component (220-1) is shown in FIG. 2A, it will be recognized that the medical device (200) may include any number of engagement components (220-1) disposed on or coupled to any location on the body of the medical device (200). For example, the medical device (200) may include two engagement components (220-1)—one on either end of the medical device (200). The medical device (200) may alternatively not include any engagement components (220-1), as will be described in more detail below.

The engagement component (220-1), as well as all other engagement components described herein, may either be permanently or temporarily coupled to the body of the implantable medical device (200). The engagement component (220-1) may alternatively be integrally formed with the body of the implantable medical device (200). The engagement component (220-1) may be made out of any suitable material. In some embodiments, the engagement component (220-1) is made out of a resorbable, absorbable, or dissolvable material.

As shown in FIG. 2A, the engagement component (220-1) includes multiple edges (230) around its perimeter. In the example of FIG. 2A, the engagement component (220-1) has a crenelated configuration with square or rectangular indentations around the perimeter of the engagement component (220-1). Within each crenellation is an engagement edge (230). These edges (230), as will be described in more detail with FIGS. 2B-2D, are configured to engage with corresponding teeth (240) located about the perimeter of the engagement tool (210-1). The engagement component (220-1) may also include a tapered edge (250) along its external perimeter that is configured to expand the teeth (240) of the engagement tool (210-1) as the teeth (240) first begin to engage with the engagement component (220-1). Additionally or alternatively, the engagement tool (210-1) may include a tapered edge (260) along the internal perimeter of the teeth (240). The tapered edge (260) may also be configured to expand the teeth (240) of the engagement tool (210-1) as the teeth (240) first begin to engage with the engagement component (220-1).

FIG. 2B is a cross-sectional close-up view of a tooth (240) of the engagement tool (210-1) prior to engaging with one of the edges (230) of the engagement component (220-1). To engage the tooth (240) with the edge (230), the engagement tool (210-1) may be advanced through the cannula 110 (FIG. 1) towards the implanted medical device (200).

FIG. 2C is a cross-sectional close-up view of the tooth (240) as it is engaging with the edge (230) of the engagement component (220-1). As the tooth (240) comes in contact with the edge (230), the tapered edge (260) of the tooth (240) slides against the tapered edge (250) of the engagement component (220-1), which causes the tooth (240) to slide over the edge (260) and lock into position in a crenellation of the engagement component (220-1).

FIG. 2D is a cross-sectional close-up view of the tooth (240) after it has been engaged with the edge (230) of the engagement component (220-1). The tooth (240) is slid past the edge (230) until the tooth (240) locks into position with the edge (230).

As shown in FIG. 2D and in FIG. 2A, the edges (230) of the engagement component (220-1) and the teeth (240) of the engagement tool (210-1) may be formed so as to laterally lock against each other and prevent movement between the implanted medical device (200) and the engagement tool (210-1). Thus, rotating the engagement tool (210-1) causes the implanted medical device (200) to rotate. Similarly, linear movement of the engagement tool (210-1) causes linear movement of the implanted medical device (2000. In this manner, the engagement tool (210-1) may be rotated to release the device (200) from any surrounding tissue that may be attached to the device (200). The device (200) may then be explanted from the patient by retracting the engagement tool (210-1) from the patient.

In some embodiments, after the engagement tool (210-1) is fully engaged with the implanted device (200), the cannula 110 (FIG. 1) may be slid over the teeth (240) of engagement tool (210-1) to prevent the teeth (240) from becoming disengaged from the crenellated edges (230). Thus, when the cannula (110) is not surrounding the teeth (240), the tool (210-1) may be removed from the implanted medical device (200). This may be advantageous when the positioning of the implanted medical device (200) is to be adjusted within the patient. Alternatively, the teeth (240) and/or corresponding edges (230) may be tapered at their distal edges to prevent the teeth (240) from becoming disengaged from the edges (230).

Figure 3A:
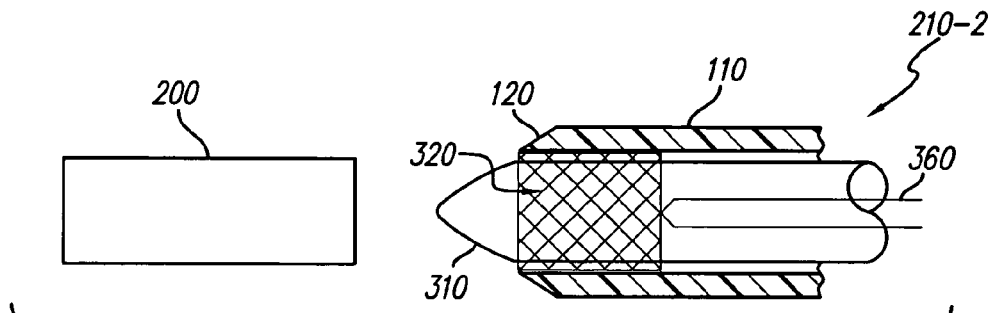
FIG. 3A is a cross-sectional view of a cannula and a side view of a needle and net that may comprise an engagement tool according to principles described herein.

FIG. 3A illustrates a cannula (110), needle (310), and net (320) that may comprise an engagement tool (210-2) that is used to explant an implanted medical device (200). The engagement tool (210-2) may include any combination of the cannula (110), needle (310), and net (320). In some embodiments, the cannula (110) is part of a syringe needle. The needle (310) may have a relatively blunt end with tapered sides so as to spread, rather than cut, tissue as the engagement tool (210-2) is advanced into the patient.

As will be described in connection with FIGS. 3B-3D, the net (320) is configured to be placed around the implanted medical device (200). Wires (360) may then be pulled by the surgeon to contract or tighten the net around the implanted device (200). Once the net (320) has been tightened around the device (200), the device (200) may be pulled into the cannula (110). The wires (360) and net (320) may be constructed of any suitably strong material that can be placed around the implanted device (200) and then used to explant the implanted device (200) from the patient. For example, the wires (360) and net (320) may be made out of thread, suture string, or any other suitable metal or fibrous material. In some embodiments, the wires (360) so that they can be used to advance the net (320) towards the implanted medical device (200).

Figure 3B:
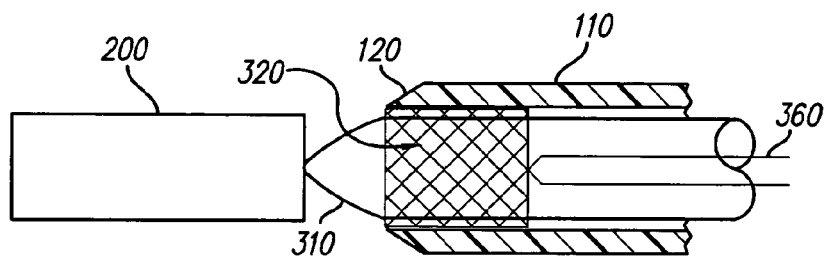
FIG. 3B is a cross-sectional view of the cannula and a side view of the needle and net prior to engaging with the implantable medical device according to principles described herein.

FIG. 3B is a cross-sectional view of the cannula (110) and a side view of the needle (310) and net (320) prior to engaging with the implanted medical device (200). The engagement tool (210-2) is advanced towards the implanted device (200) until the blunt needle (310) comes into contact with the implanted device (200). The net (320) may then be advanced towards the device (200) using the wires (360; FIG. 3A), the cannula (110) or some other means for advancing the net (320) and slid around the outer surface of the implanted device (200). The needle (310) may be retracted before, during, or after the advancement of the net (320).

Figure 3C:
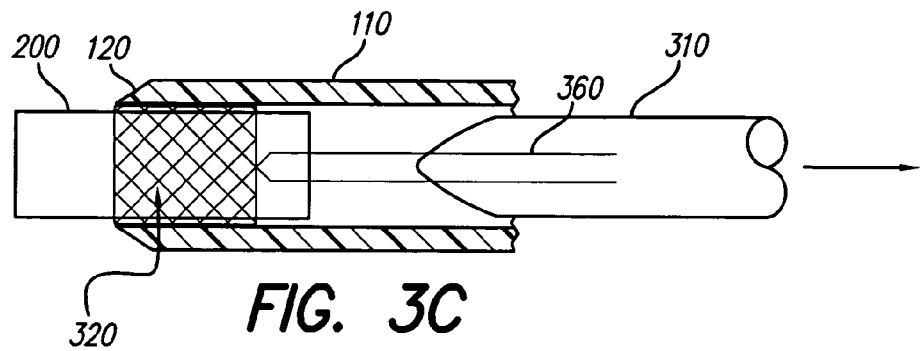
FIG. 3C is a cross-sectional view showing the net engaged with the implantable medical device according to principles described herein.

In some embodiments, as shown in FIG. 3C, the cannula (110) is used to advance the net (320) to engage the implanted medical device (200). The cannula (110) may be advanced so as to partially or completely surround the implanted medical device (200). A hook or some other structure on the inner surface of the cannula (110) may be configured to snag the net (320) as the cannula (110) is being advanced. The net (320) is then dragged along and advanced with the cannula (110). In this manner, the net (320) can engage with the implanted medical device (200). As the net (320) is advanced, the net (320) is slipped or slid around the outer surface of the implanted medical device (200). The needle (310) may be retracted before, during, or after the advancement of the net (320).

FIG. 3C shows the net (320) engaged with the implantable medical device (200). In some embodiments, the surgeon may pull on the wires (360) to tighten the net (320) and/or explant the implanted device (200) from the patient. In some alternative embodiments, as shown in FIG. 3C, the wires (360) may be attached to the needle (310). As the wires (360) and/or needle (310) is retracted, the net (320) tightens around the outer surface of the device (200). The device (200) may then be pulled through the lumen of the cannula (110) and removed from the patient. In some alternative embodiments, the device (200) does not pass through the lumen of the cannula (110). This permits the cannula (110) to have an inner diameter, and potentially outer diameter, smaller than the outer diameter of the device (200).

Figure 3D:
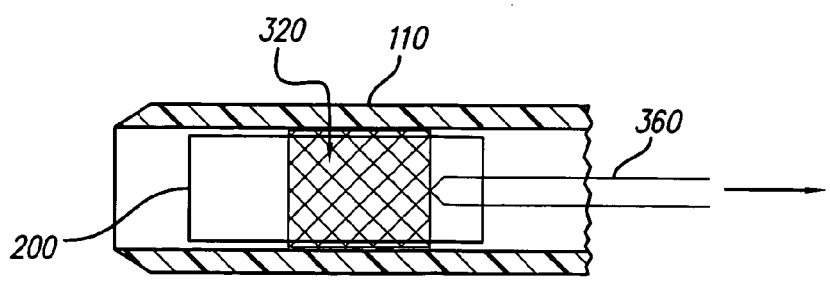
FIG. 3D is a cross-sectional view of the cannula and a side view of the net engaged with the implantable medical device according to principles described herein.

FIG. 3D is a cross-section view of the cannula (110) and a side view of the net (320) engaged with the implantable medical device (200) which has been drawn into the cannula (110). A surgeon may remove the device (200) from the patient by pulling the wires (360) and/or needle (310) connected to the wires (360) to draw the device (200) into and through the cannula (110). As the device (200) enters the cannula (110), the cutting edge (120) of the cannula (110) may serve to cut away tissue that is attached to the device (200).

Figure 4A:
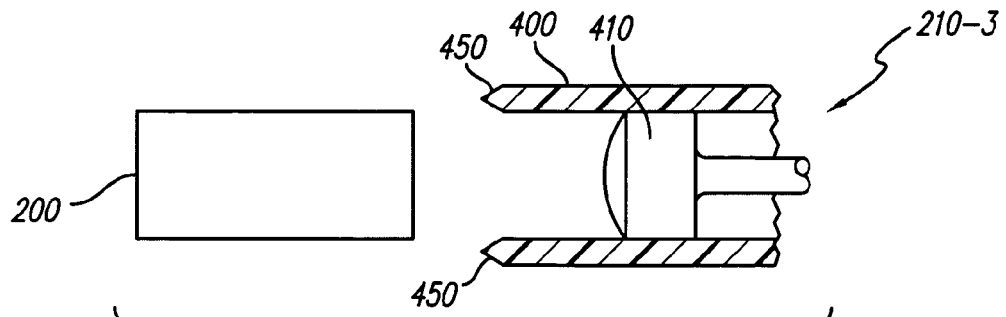
FIG. 4A is a cross-sectional view of a cannula and a plunger that may be used as an engagement tool according to principles described herein.

FIG. 4A illustrates a cannula (400) and a plunger (410) that may be used as an engagement tool (210-3) that is used to extract an implanted medical device (200). The cannula (400) and plunger (410) may form a syringe device configured to extract the implanted device (200) from the patient through the use of suction created with a liquid vacuum. The plunger (410) is configured to fit within the lumen of the cannula (400) so as to create a vacuum when the plunger (410) is retracted within the cannula (400). The inner diameter of the cannula (400) is slightly larger than the outer diameter of the device (200) so as to retain the vacuum pressure as the device (200) is sucked by vacuum into the lumen of the cannula (400).

Figure 4B:
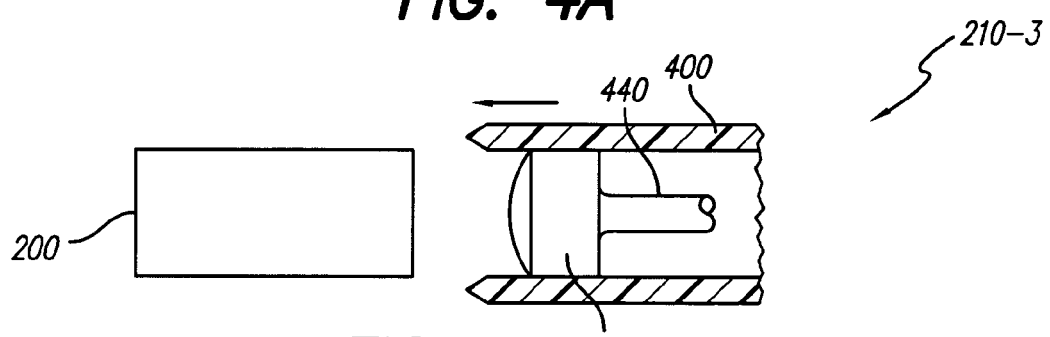
FIG. 4B is a cross-sectional view of the cannula, plunger, and implantable medical device of FIG. 4A prior to engagement according to principles described herein.

FIG. 4B is a cross-sectional view of the cannula (400), plunger (410), and implantable medical device (200) of FIG. 4A prior to engagement. The engagement tool (210-3) and cannula (400) may be advanced until the cannula (400) and/or plunger (410) is proximate to, or in contact with, the implanted medical device (200).

Figure 4C:
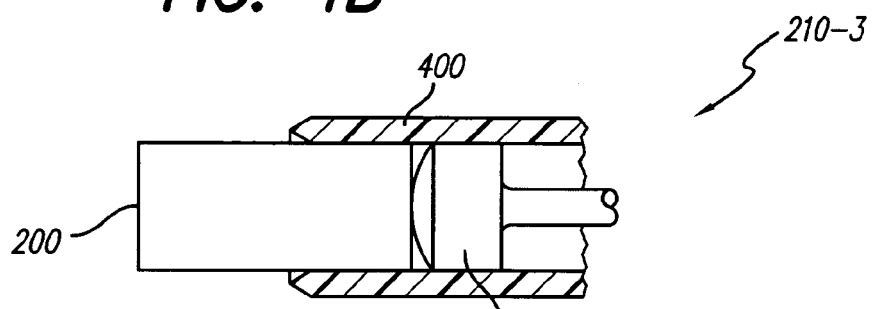
FIG. 4C is a cross-sectional view of the cannula and plunger engaging with the implantable medical device of FIG. 4B according to principles described herein.

FIG. 4C is a cross-sectional view of the cannula (400) and plunger (410) engaging or in contact with the implantable medical device (200) of FIG. 4B. In this positioning, a vacuum can be created with movement of the plunger (410) to draw the implanted device (200) at least partially into the cannula (400).

Figure 4D:
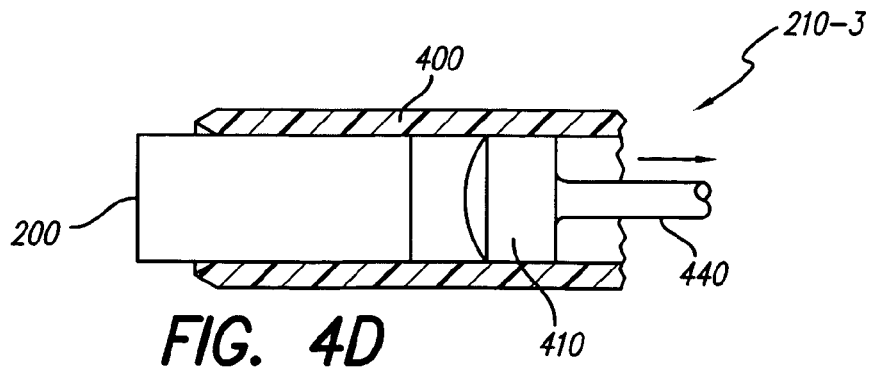
FIG. 4D is a cross-sectional view of the cannula and plunger as the medical device is being sucked into the lumen of the cannula according to principles described herein.

FIG. 4D is a cross-sectional view of the cannula (400) and plunger (410) as the medical device (200) is being drawn into the lumen of the cannula (400). As the plunger (410) is retracted, a vacuum is created within the cannula in the space through which the plunger has been withdrawn. Under the influence of this vacuum, the device (200) is pulled into the lumen of the cannula (400). One or more cutting edges (450) at the proximal end of the cannula (400) may serve to cut away tissue that may be attached to the device (200).

Figure 5A:
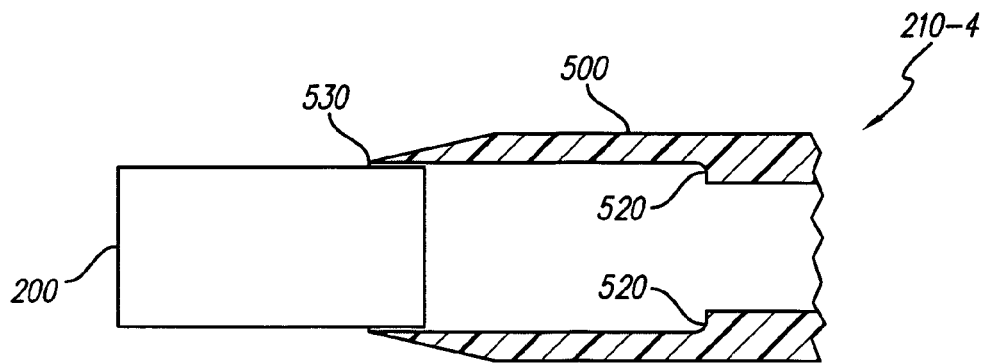
FIG. 5A is a cross-sectional view of a cannula that may be used as an engagement tool according to principles described herein.

FIG. 5A is a cross-sectional view of a cannula (500) that may be used as an engagement tool (210-4) that is used to extract an implanted medical device (200). As shown in FIG. 5A, the cannula (500) may include one or more shelves (520) formed in, or coupled to, its inner surface. The shelves (520) are configured to prevent the device (200) from advancing beyond a pre-determined point within the cannula (500). The shelves (520) also prevent the cutting edges (530) of the cannula (500) from reaching beyond the distal end of the implanted device (200) and damaging tissue located beyond the distal end of the implanted device (200). The cutting edges (530) serve to cut tissue away from the outer surface of the device (200) to facilitate explantation of the medical device (200).

The cannula (500) of FIG. 5A may be used in connection with the syringe device described in connection with FIGS. 4A-4D and may be filled with a fluid or other suitable substance, such as a saline solution or air. Once the cannula (500) is positioned proximate to the implanted medical device (200), for example, in the orientation shown in FIG. 5A, the fluid in the cannula is withdrawn, for example, with a pump, plunger or the like. The fluid withdrawing from the cannula (500) creates a vacuum in the cannula (500) that is used to pull the device (200) into position within the cannula (500).

In some alternative embodiments, the shelves (520) may include an adhesive substance, such as a medical glue, configured to adhere to the implanted medical device (200). Once the shelves (520) have been adhesively attached to the device (200), the cannula (500) may be retracted to explant the implanted device (200).

Figure 5B:
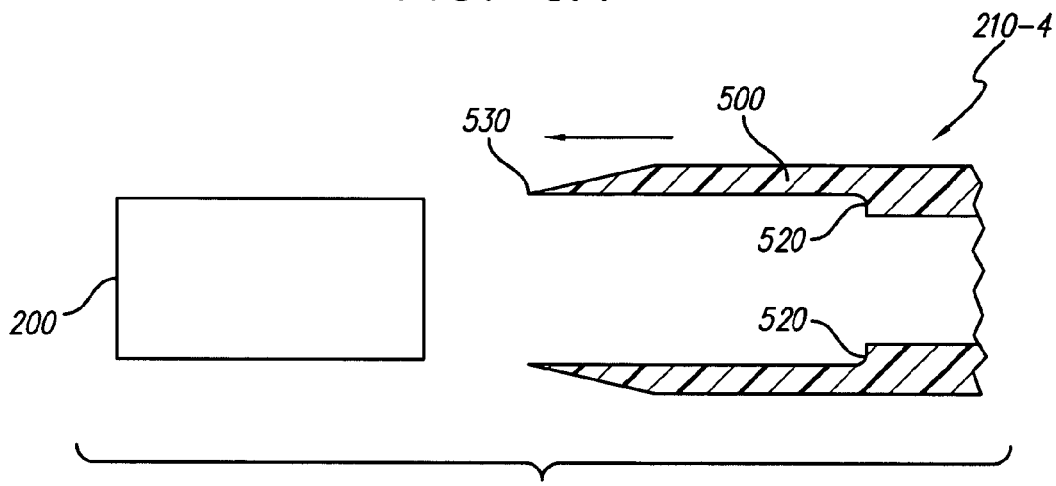
FIG. 5B is a cross-sectional view of the cannula of FIG. 5A prior to engaging with the implanted medical device according to principles described herein.

FIG. 5B is a cross-sectional view of the cannula (500) of FIG. 5A prior to engaging with the implanted medical device (200). The cannula (500) is advanced towards the device (200) and the sharp edges (530) may cut surrounding tissue away from the device (200) as the cannula (500) slides over and around the outer surface of the device (200). A suction force may simultaneously or alternatively pull the device (200) into the lumen of the cannula (500).

Figure 5C:
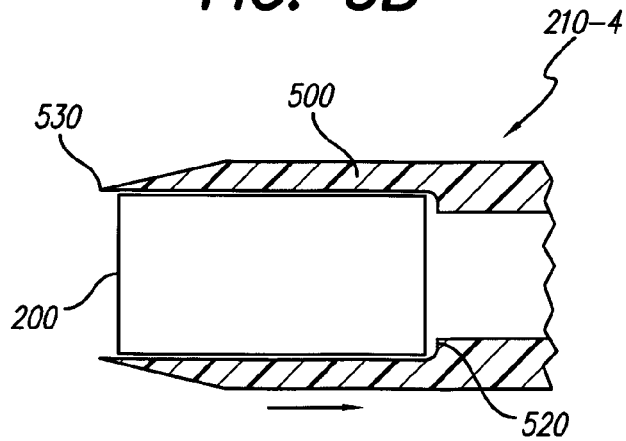
FIG. 5C is a cross-sectional view of the cannula engaged with the implantable medical device according to principles described herein.

FIG. 5C is a cross-sectional view of the cannula (500) engaged with the implanted medical device (200). As shown in FIG. 5C, the proximal end of the device (200) has been prevented by the shelves (520) from advancing further into the lumen of the cannula (500).

Figure 6:
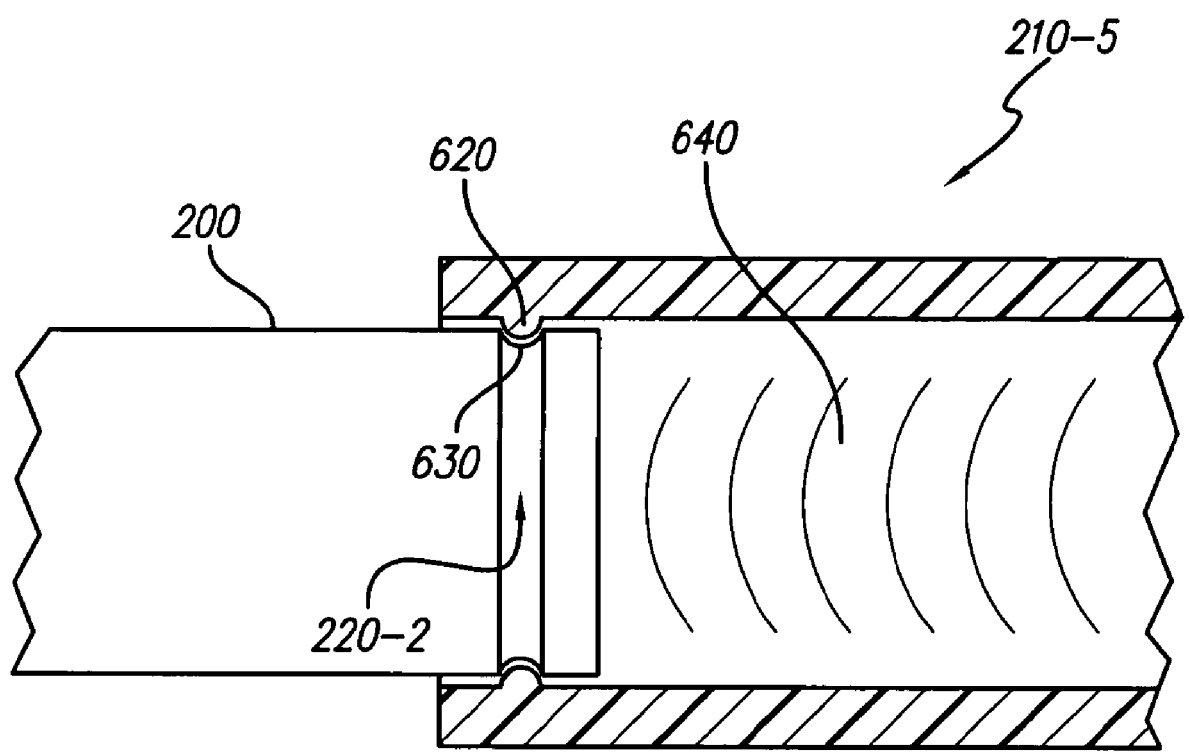
FIG. 6 is a cross-sectional view of another exemplary engagement tool according to principles described herein.

FIG. 6 is a cross-sectional view of another exemplary engagement tool (210-5) that is coupled to an implantable medical device (200). As shown in FIG. 6, the engagement tool (210-5) includes one or more convex members (620) along its inner surface configured to engage with a corresponding concave engagement component (220-2) that is a part of, or disposed on, the implantable medical device (200). The engagement component (220-2) of FIG. 6 includes one or more concave notches (630) configured to engage with the one or more convex members (620). In some embodiments, the device (200) may be extracted from the patient once the convex members (620) have engaged with the concave notches (630).

Additionally or alternatively, the engagement tool (210-5) may include fluid (640) within its lumen. A surgeon may use a device external to the body of the patient to transfer ultrasonic energy through the fluid (640) to the proximal end of the device (200) in order to shake the device (200) loose from surrounding tissue that may have attached to the device (200). Shaking the device (200) loose from surrounding tissue, rather than cutting the tissue away from the device (200), avoids undesirable bleeding, scarring, and other tissue damage that may occur when the tissue is cut.

Figure 7A:
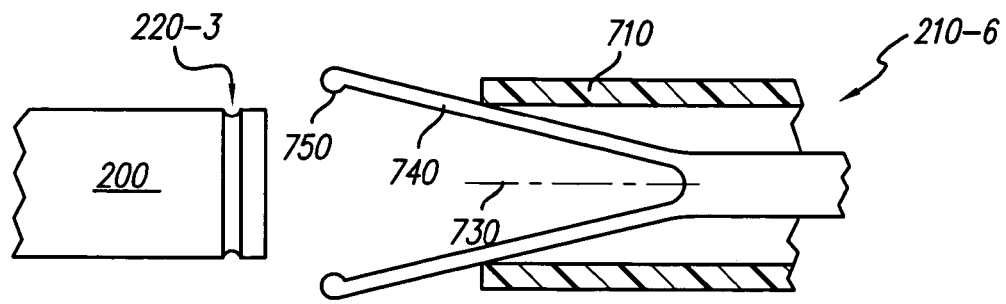
FIG. 7A is a cross-sectional view of another exemplary engagement tool and cannula according to principles described herein.

FIG. 7A is a cross-sectional view of another exemplary engagement tool (210-6) and cannula (710) that may be used to explant an implanted medical device (200). The engagement tool (210-6) includes two arms (740) configured in a tweezer-like configuration. The arms (740) are flexible, but biased to a open position illustrated in FIG. 7A in which the arms (740) naturally spread apart from each other as they extend from the cannula (710). Each arm (740) includes a gripping device (750) at its proximal end configured to engage with a corresponding engagement component (220-3) that is disposed on or coupled to the implanted medical device (200). The gripping device (750) may be any suitable device or structure configured to engage with the engagement component (220-3) and may include, but is not limited to, at least one or more of a convex member, block, tooth, hook, serration, and adhesive. Likewise, the engagement component (220-3) may include any device or structure configured to engage with the gripping device (750). For example, the engagement component (220-3) may include concave notches (760), as shown in FIG. 7A. The engagement component (220-3) may additionally or alternatively include at least one or more of a convex member, block, tooth, serration, adhesive, or any other suitable structure or device.

In some embodiments, the gripping devices (750) may be configured to free the implanted medical device (200) from surrounding tissue. For example, the gripping devices (750) may include one or more sharp edges configured to cut through tissue that is attached to the implanted medical device (200). Additionally or alternatively, the gripping devices (750) may be configured to heat up to facilitate the removal or the medical device (200) from surrounding tissue.

Figure 7B:
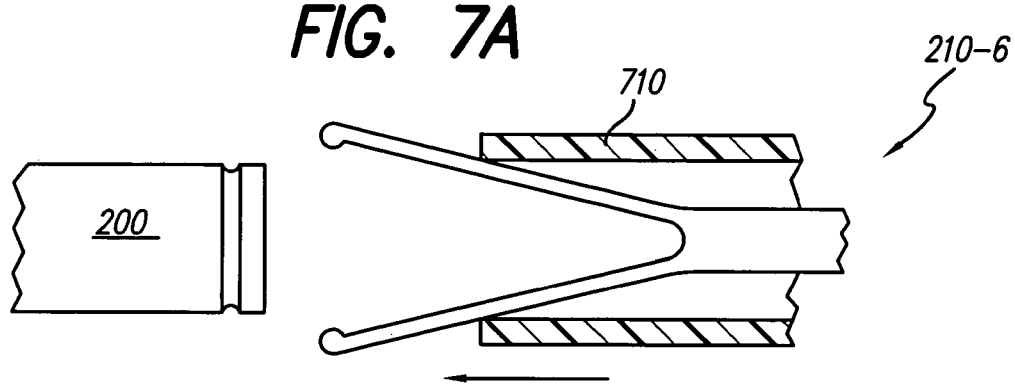
FIG. 7B is a cross-sectional view of the engagement tool and cannula of FIG. 7A prior to engaging with the implanted medical device according to principles described herein.

FIG. 7B is a cross-sectional view of the engagement tool (210-6) and cannula (710) prior to engaging with the implanted medical device (200). When the cannula (710) has been advanced to a position suitably close to the implanted medical device (220), the engagement tool (210-6) may be advanced from the proximal end of the cannula (710). The arms (740) of the engagement tool (210-6) are biased to bend away from a central axis (730). Hence, as the engagement tool (210-6) is advanced, the arms (740) open, expanding away from the central axis (730).

Figure 7C:
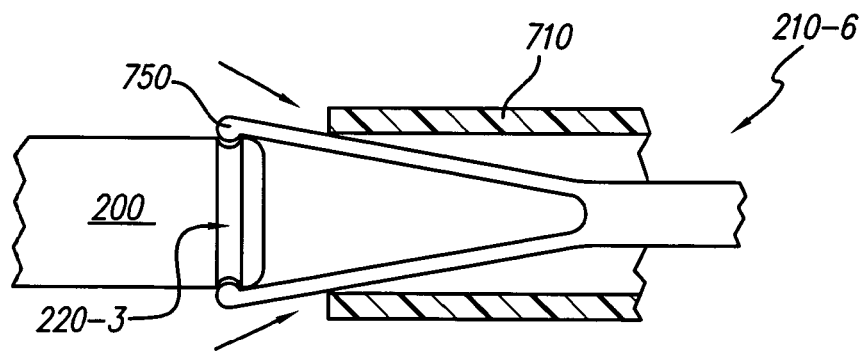
FIG. 7C is a cross-sectional view of the engagement tool of FIG. 7A engaging with the implanted medical device according to principles described herein.

FIG. 7C is a cross-sectional view of the engagement tool (210-6) engaging with the implanted medical device (200). The position of the arms (740) may be adjusted by the surgeon as necessary to engage with the engagement component (220-3). The engagement tool (210-6) may automatically engage with the engagement component (220-3) when the arms (740) pass over the engagement component (220-3). Additionally or alternatively, the arms (740) may be closed or clamped on the engagement component (220-3) by advancing the cannula (710) relative to the arms (740) when the arms (740) are positioned around the engagement component (220-3).

Figure 7D:
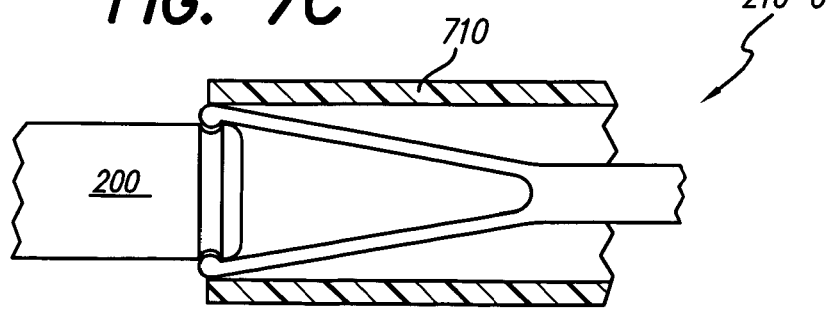
FIG. 7D is a cross-sectional view of the engagement tool of FIG. 7A fully engaged with the implantable medical device according to principles described herein.

FIG. 7D is a cross-sectional view of the engagement tool (210-6) fully engaged with the implantable medical device (200). In some embodiments, the device (200) does not fully retract into the lumen of the cannula (710) because the inner diameter of the cannula (710) is smaller than the outer diameter of the engagement tool (210-6) when fully engaged with the device (200). Alternatively, the inner diameter of the cannula (710) may be enlarged slightly to allow the engagement tool (210-6) to pull the device (200) into the lumen of the cannula (710). Thus, the device (200) may be extracted from the patient through the lumen of the cannula (710) without removing the cannula (710).

Figure 7E:
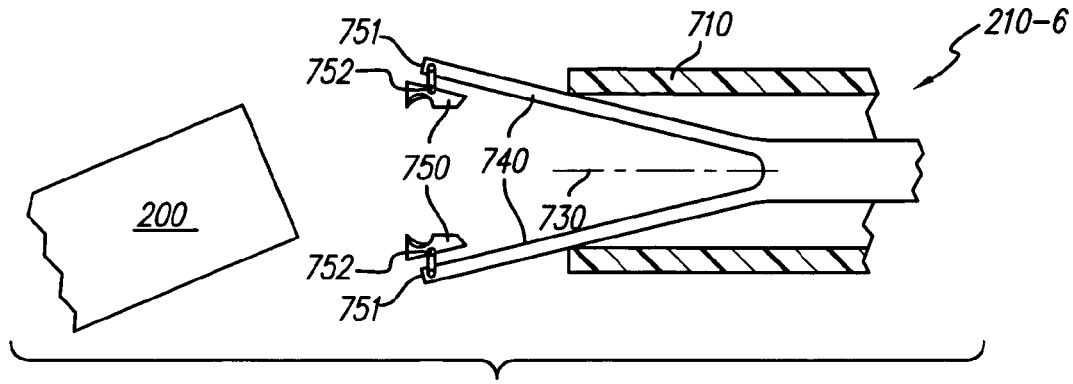
FIG. 7E is a cross-sectional view showing that the gripping devices of the engagement tool of FIG. 7A may be configured to rotate about any axis according to principles described herein.

FIG. 7E shows that the gripping devices (750) may be configured to rotate about any axis. In some embodiments, as shown in FIG. 7E, there may be multiple points (751, 752) of rotation. These points of rotation (751, 752) may include hinges, ball and socket joints, or any other type of rotation mechanism.

Figure 7F:
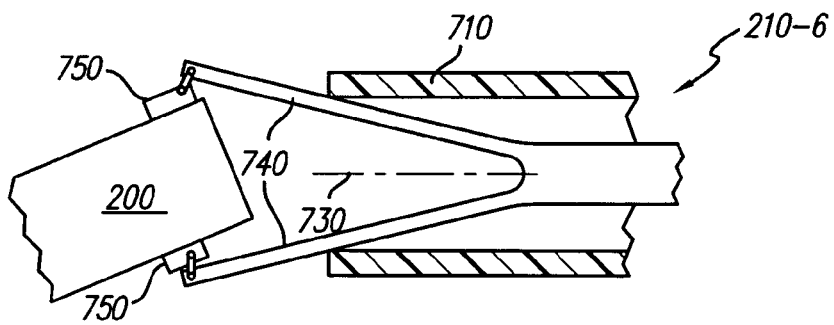
FIG. 7F is a cross-sectional view showing the rotatable gripping devices of FIG. 7E coupled to the implanted medical device according to principles described herein.
Figure 7G:
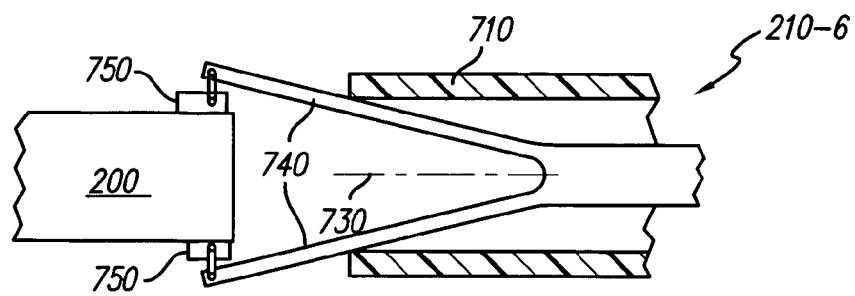
FIG. 7G is a cross-sectional view showing the implanted medical device after it has become aligned with the central axis of the engagement tool of FIG. 7F according to principles described herein.

Rotatable gripping devices (750) are advantageous when the entry path or central axis (730) of the engagement tool (210-6) is not aligned with the length of the implanted medical device (200), as shown in FIG. 7E. However, the rotatable gripping devices (750) may still be coupled to the implanted medical device (200), as shown in FIG. 7F. Once the rotatable gripping devices (750) are coupled to the implanted medical device (200), the engagement tool (210-6) may be retracted. As the engagement tool (210-6) is retracted, the implanted medical device (200) becomes aligned with the central axis (730), as shown in FIG. 7G. The engagement tool (210-6) may then be further retracted to extract the implanted medical device (200).

FIG. 8A is a perspective view of another exemplary engagement tool (210-7). As will be described in more detail in connection with FIGS. 8B-8D, the engagement tool (210-7) of FIG. 8A includes a clamping member (810) configured to clamp onto or engage with an implantable medical device (200). As shown in FIG. 8A, the clamping member (810) opens and closes by rotating around an axis, such as hinge (830). An adjustment device (820) may be coupled to the clamping member (810) and/or the hinge (830) so that the surgeon may open and close the clamping member (810). The adjustment device (820) may be an actuator, wire, string, mechanical device, motor, or any other device configured to open and/or close the clamping member (810).

FIG. 8B is a close-up view of the clamping member (810) in a closed position. When closed, the clamping member (810) may overlap slightly with a corresponding edge (850) of the engagement tool (210-7). Alternatively, the clamping member (810) may be substantially flush with the edge (850) of the engagement tool (210-7).

The inner surface of the engagement tool (210-7), including the clamping member (810), and/or the outer surface of the implantable medical device (200) may include any of a number of substances and/or structures configured to adhesively attach or couple the engagement tool (210-7) to the medical device (200) when the clamping member (810) clamps onto or engages with the medical device (200). For example, the inner surface of the engagement tool (210-7) may be gritty, sandy, or rough and/or may include glue, adhesive material or substance(s), Velcro™, spike(s), hook(s), bump(s), nub(s), thread(s), and/or any other material or structure configured to adhesively couple the engagement tool (210-7) with the medical device (200).

FIG. 8C is a side view of the engagement tool (210-7) prior to engaging with an implantable medical device (200). As shown in FIG. 8C, the clamping member (810) is in an open position. The engagement tool (210-7) is maneuvered until the implanted medical device (200) becomes situated within the cavity of the engagement tool (210-7). The clamping member (810) may then be closed to clamp onto or engage with the implanted medical device (200).

FIG. 8D is a side view of the engagement tool (210-7) fully engaged with the implanted medical device (200). With the clamping member (820) closed around the implanted medical device (200), the engagement tool (210-7) may be retracted to explant the medical device (200).

Figure 9A:
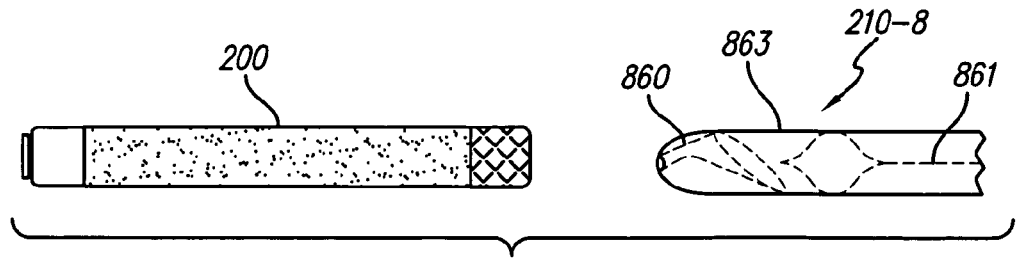
FIG. 9A is a side view of another exemplary engagement tool according to principles described herein.

FIG. 9A is a side view of another exemplary engagement tool (210-8). The engagement tool (210-8) is shown approaching an implantable medical device (200). The engagement tool (210-8) includes a central lumen (863) through which a loop or lasso (861) is passed to engage the implanted medical device (200). The lumen (863) of the engagement tool (210-8) includes a tapered neck (860) configured to compress the loop (861) as the loop (861) is advanced through the lumen (863) of the engagement tool (210-8) and into the neck (860). The neck (860) is angled so as to permit the loop (861) to exit the neck (860) at an angle suitable for engaging with the implanted medical device (200).

Figure 9B:
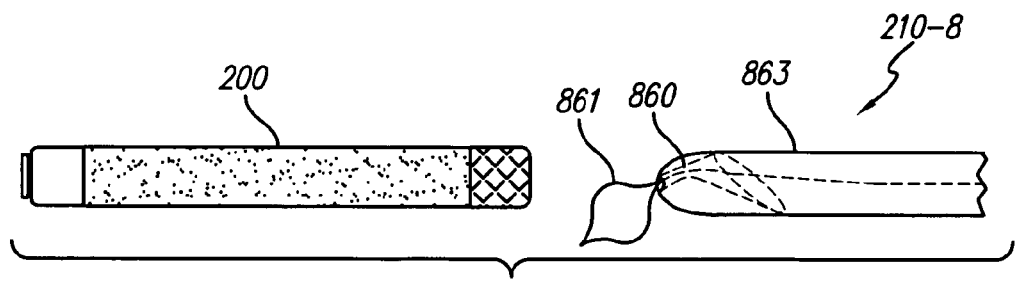
FIG. 9B is a side view of the engagement tool of FIG. 9A prior to engagement with the implantable medical device according to principles described herein.

The loop (861) is biased, or preformed, toward the open position so that when no other force is exerted on the loop (861), the loop (861) is fully opened, as shown in FIG. 9B. The loop (861) may be made out of wire (e.g., any metal based wire), string, or any other material suitable for engaging with the implanted medical device (200). The loop (861) may additionally or alternatively include a sharp edge for cutting through tissue.

FIG. 9B is a side view of the engagement tool (210-8) prior to engagement with the implantable medical device (200). As shown in FIG. 9B, the loop (861) has been advanced out of the neck (860) and may emerge at an angle with respect to the central axis of the engagement tool (210-8).

Figure 9C:
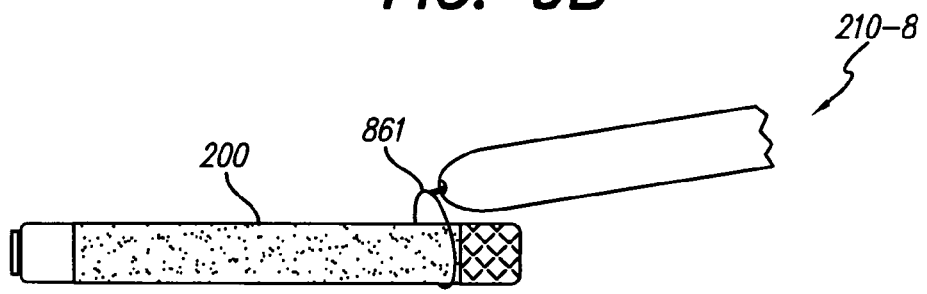
FIG. 9C is a side view of the engagement tool of FIG. 9A engaging with the implantable medical device according to principles described herein.

FIG. 9C is a side view of the engagement tool (210-8) engaging with the implantable medical device (200). As a surgeon advances the engagement tool (210-8) towards the device, the loop (861) surrounds the outer surface of the implanted device (200). The surgeon may then tighten or close the loop (861) around the implanted device (200). In some embodiments, the loop (861) may be slid along the entire length of the device (200) to cut surrounding tissue from the implanted device (200).

Figure 9D:
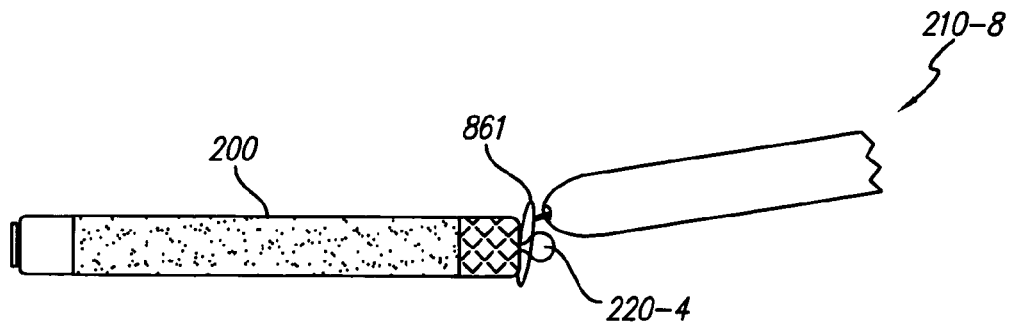
FIG. 9D is a side view illustrating an engagement component configured to engage with the engagement tool of FIG. 9A according to principles described herein.

In some embodiments, as shown in FIG. 9D, the implantable medical device (200) may include an engagement component (220-4) configured to engage with the loop (861). The engagement component (220-4) may be any engagement component (220) described herein. For example, the engagement component (220-4) may include a ball and neck (as shown in FIG. 9D), a hook, or any other structure configured to couple with the loop (861).

Figure 9E:
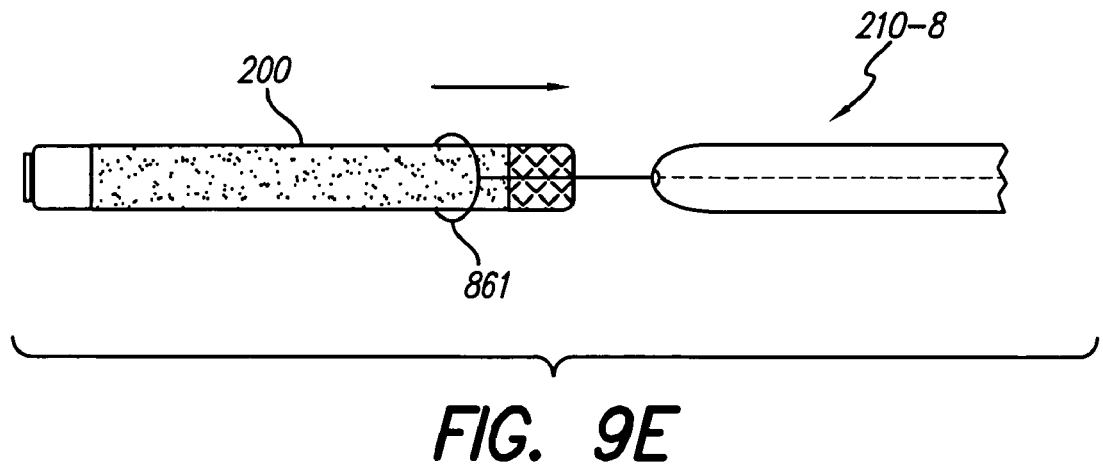
FIG. 9E is a side view of the engagement tool of FIG. 9A engaged with the implantable medical device according to principles described herein.

FIG. 9E is a side view of the engagement tool (210-8) engaged with the implantable medical device (200). Once the loop (861) has been tightened around the implanted device (200), the engagement tool (210-8) may be retracted to explant the medical device (220).

Figure 9F:
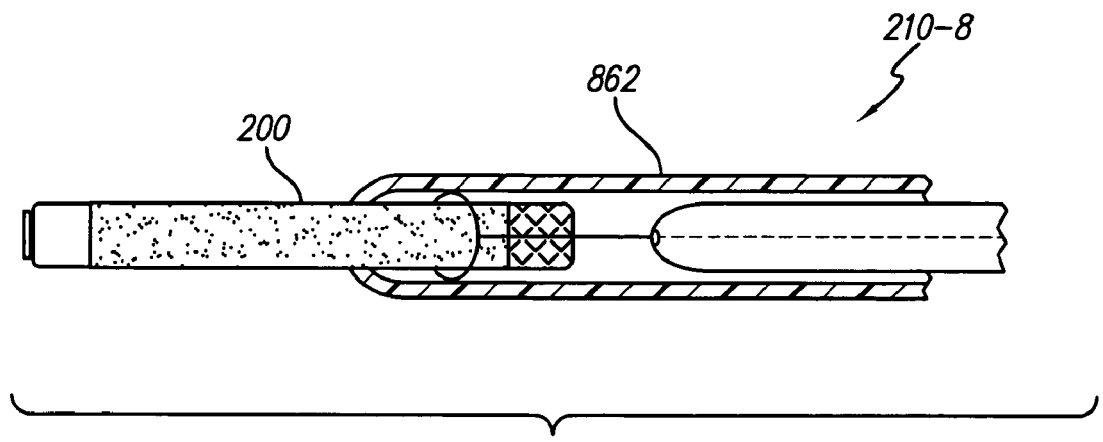
FIG. 9F is a side view showing that the engagement tool of FIG. 9A may be advanced towards the implanted medical device through the lumen of a cannula according to principles described herein.

FIG. 9F shows that the engagement tool (210-8) may be advanced towards the implanted medical device (200) through the lumen of a cannula (862). Once the loop (861) is engaged with the medical device (200), the engagement tool (210-8) may be retracted through the lumen of the cannula (862) to explant the medical device (220). The cannula (862) may be similar to any of the cannulas described herein.

A number of additional or alternative engagement components (220) will be described in connection with FIGS. 10-18. These engagement components (220) may be used in connection with any of the engagement tools (210) described herein or with other engagement tools specifically adapted to correspond to the described engagement components (220). The examples given herein to help describe the function of the engagement components (220) describe various methods of explanting an implanted medical device (200) from a patient. However, it will be recognized that the engagement components may be additionally or alternatively used to engage, manipulate, move, reposition, interconnect, or implant an implantable medical device.

Figure 10:
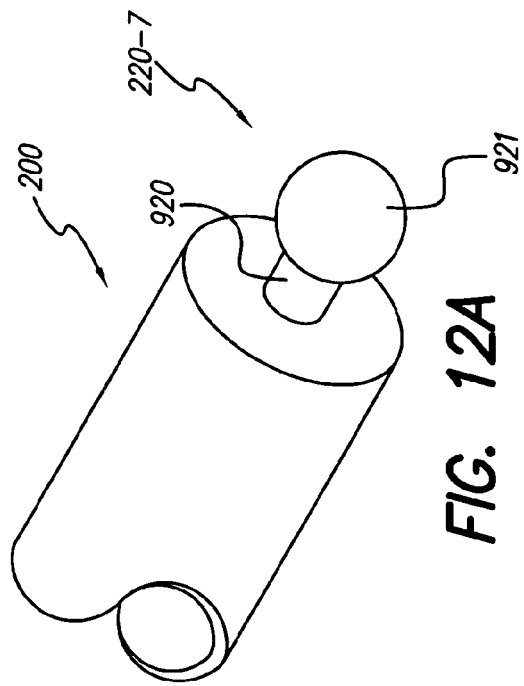
FIG. 10 is a perspective view of an exemplary engagement component according to principles described herein.

FIG. 10 is a perspective view of one exemplary engagement component (220-5) that is part of an implantable medical device (200). The engagement component (220-5) includes a female threaded cavity. The female threaded cavity is configured to engage with an engagement tool having a corresponding male threaded member. The engagement tool is inserted to the site of the implanted medical device (200), for example, through a cannula. The engagement tool is then rotated to thread into the female threaded cavity of the engagement component (220-5). The engagement tool is thus connected to the implanted medical device (200) and can then be used to explant or reposition the device (200).

Figure 11:
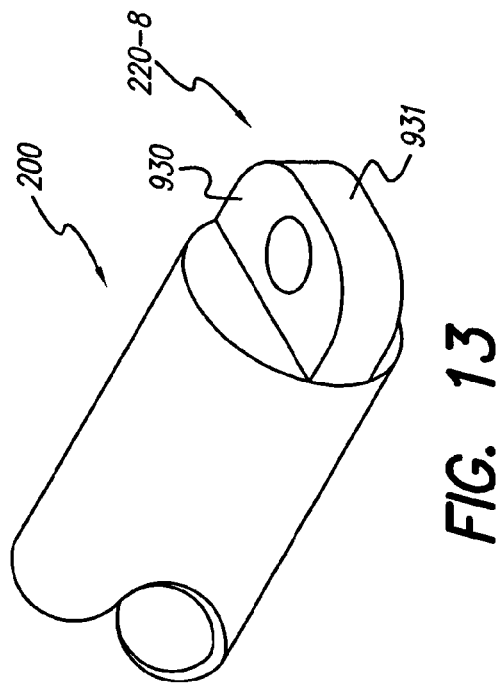
FIG. 11 is a perspective view of another exemplary engagement component according to principles described herein.

FIG. 11 is a perspective view of another exemplary engagement component (220-6) that is coupled to an implantable medical device (200). The engagement component (220-6) includes a male threaded member. The male threaded member is configured to engage with an engagement tool having a corresponding female threaded cavity. Again, the engagement tool is inserted to the site of the implanted medical device (200), for example, through a cannula. The engagement tool is then rotated to thread the male threaded member of the engagement component (220-6) into the female cavity of the engagement tool. The engagement tool is thus connected to the implanted medical device (200) and can then be used to explant or reposition the device (200).

Figure 12A:
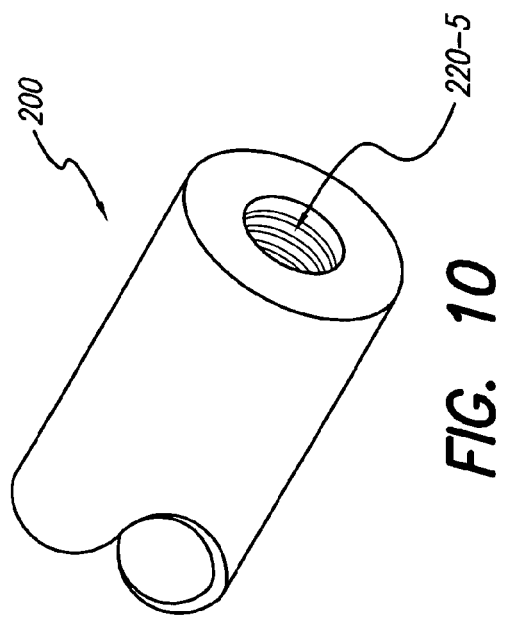
FIG. 12A is a perspective view of another exemplary engagement component according to principles described herein.

FIG. 12A is a perspective view of another exemplary engagement component (220-7) that is coupled to an implantable medical device (200). The engagement component (220-7) includes a ball (921) and neck (920) configured to engage with a number of different engagement tools as described herein or any other engagement tool specifically adapted to correspond to the engagement component (220-7). For example, as shown in FIG. 12B, the engagement component (220-7) may be configured to engage with an engagement tool (210-9) having a hole (923) with a engaging member dilates to accept the ball (921). FIG. 12C shows an end view of the hole (923) with the engaging member (924) in a closed position. As the engagement tool (210-9) comes into contact with the ball (921) of the engagement component (220-7), the engaging member (924) dilates to receive the ball (921). FIG. 12D shows the engaging member (924) in an open position. As the ball (921) is received, the engaging member (924) engages with the ball (921). In some embodiments, the inner surface (925) of the hole (923) is sharp and may be used to cut the implanted device (200) from surrounding tissue.

Figure 13:
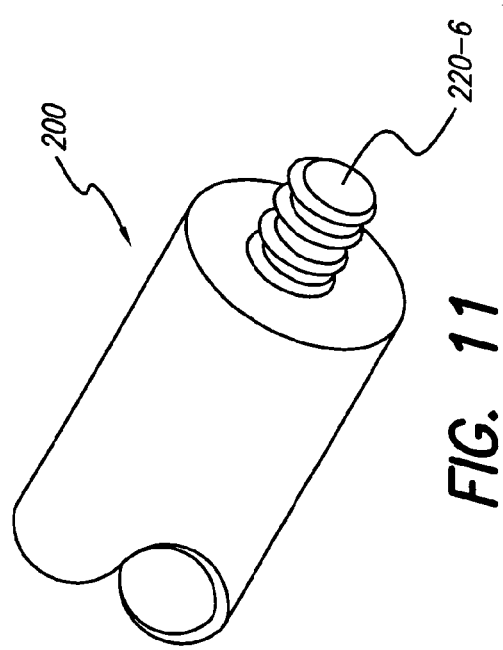
FIG. 13 is a perspective view of another exemplary engagement component according to principles described herein.

FIG. 13 is a perspective view of another exemplary engagement component (220-8) coupled to an implantable medical device (200). The engagement component (220-8) includes an outwardly extending member (931) having a hole (930)

that is configured to engage with an engagement tool having a hook, string, wire, rod, tooth, or any other suitable component.

FIG. 14A is a perspective view of another exemplary engagement component (220-9) that is a part of an implantable medical device (200). FIG. 14B is a cross-sectional view of the engagement component (220-9) of FIG. 14A. The engagement component (220-9) includes a hollow neck (941) which leads to a larger, hollow cavity (940) within the medical device (200). The engagement component (220-9) is configured to engage with an engagement tool having a hook, tooth, liquid or air inflatable balloon, reverse nubs, or any other suitable component. The engagement device of the engagement tool may pass through the neck (941) of the engagement component (220-9) and lodge in the cavity (940) so as to attach the implanted medical device (200) to the engagement tool for explantation or repositioning.

Figure 15:
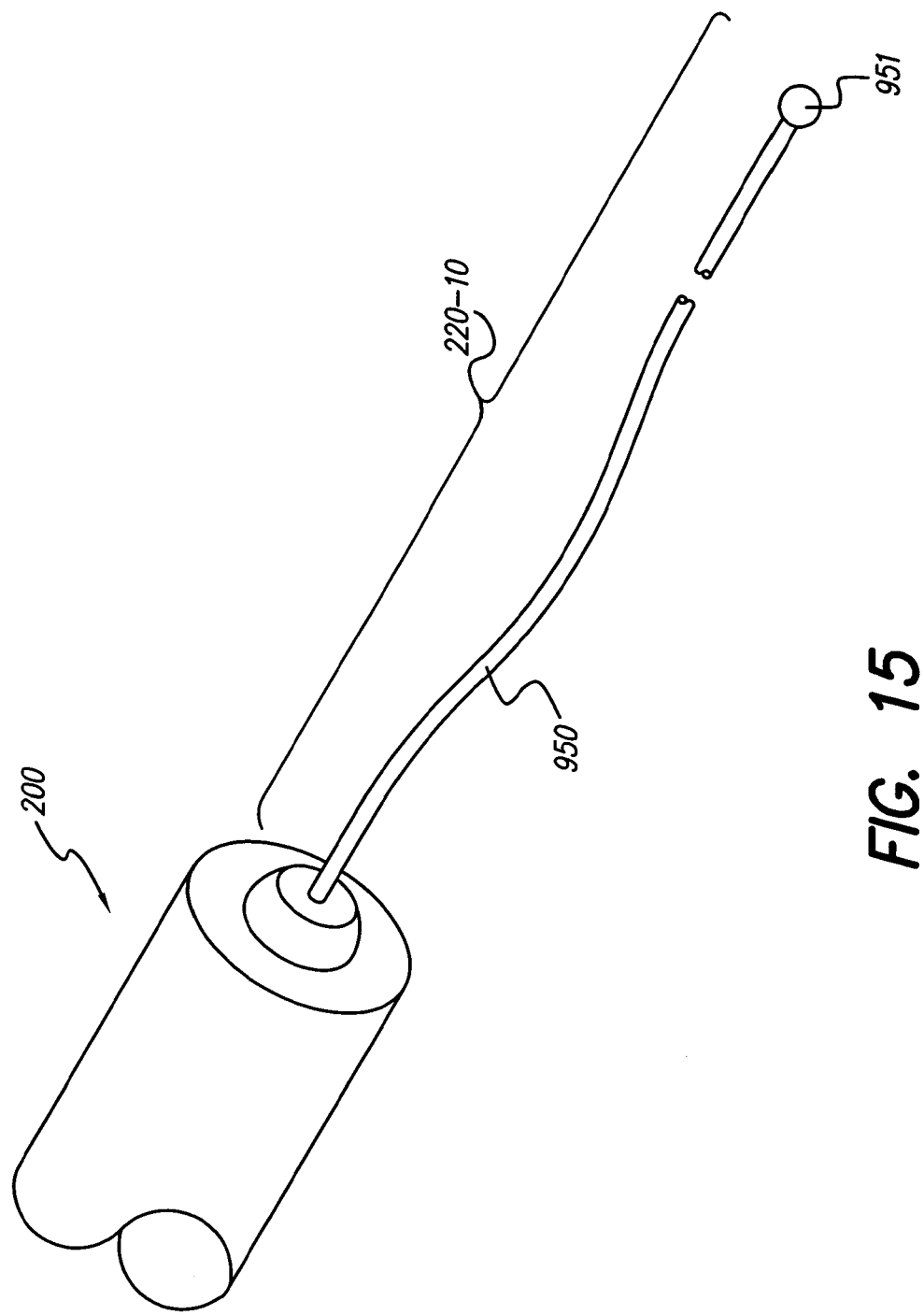
FIG. 15 is a perspective view of another exemplary engagement component according to principles described herein.

FIG. 15 is a perspective view of another exemplary engagement component (220-10) coupled to an implantable medical device (200). The engagement component (220-10) includes an engagement ball (951) coupled to the distal end of an elongated structure (950). The proximal end of the elongated structure (950) is coupled to the implantable medical device (200). The engagement ball (951) is configured to engage with a number of different engagement tools as described herein or any other engagement tool specifically adapted to correspond to the engagement component (220-10).

The elongated structure (950) may be of any suitable length and may include a tether, cord, wire, thread, ribbon, lace, line, gut, suture, or any other elongated object or structure. In some embodiments, the elongated structure (950) may be resorbable, absorbable, or dissolvable.

The elongated structure (950) and/or ball (951), as with all other structures of the various engagement components (220) described herein, may include X-ray, ultrasonic, or other identification markers that allow a surgeon to identify and/or locate the implanted medical device (200) prior to explanting or repositioning the device (200).

In some embodiments, the engagement component (220-10) may or may not include the engagement ball (951) or similar structure. The elongated structure (950) may be configured to extend away from the implanted medical device (200) to a location at or near the surface of the skin of a patient, where it may be held in place with one or more sutures or with other suitable means. The elongated structure (950) may then be used as a guide-wire over which a cannula may be threaded to extract the implanted medical device (200). Additionally or alternatively, the elongated structure (950) may be used to hold the implanted medical device (950) while an engagement tool (210) engages with the implanted medical device (950) to extract or reposition the medical device (950).

Figure 16:
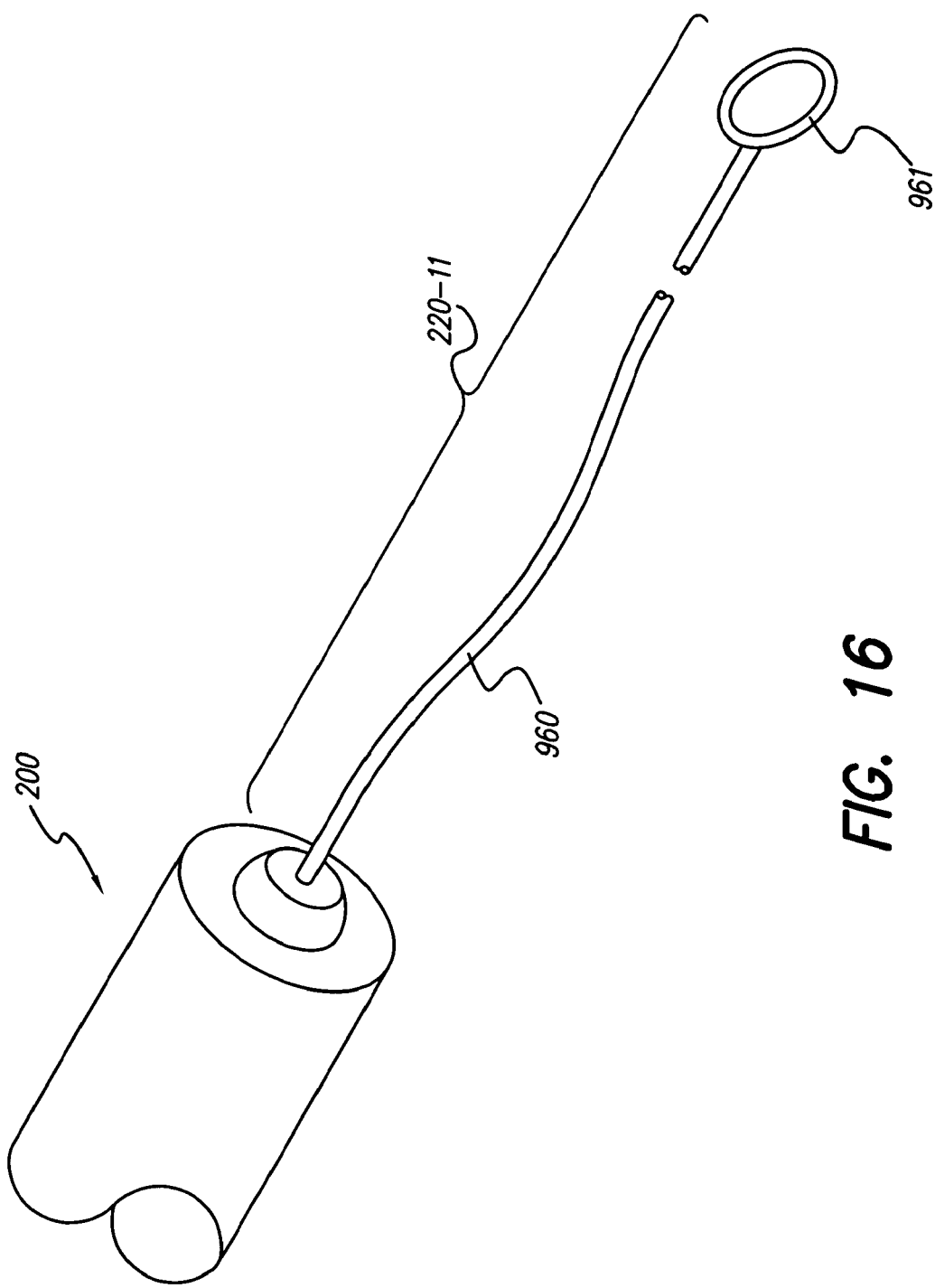
FIG. 16 is a perspective view of another exemplary engagement component according to principles described herein.

FIG. 16 is a perspective view of another exemplary engagement component (220-11) of an implantable medical device (200). The engagement component (220-11) includes an engaging ring (961) coupled to the distal end of an elongated structure (960). The proximal end of the elongated structure (960) is coupled to the implantable medical device (200). The engaging ring (961) is configured to engage with a number of different engagement tools as described herein. The engagement ring (961) of FIG. 16 and the engaging ball (951) of FIG. 15 are merely illustrative of the many different structures that may be coupled to the medical device (200) with an elongated structure (960).

The elongated structure (960) may be of any suitable length and may include a cord, wire, thread, ribbon, lace, line, gut, suture, or any other elongated object or structure. In some embodiments, the elongated structure (960) may be resorbable, absorbable, or dissolvable.

Figure 17:
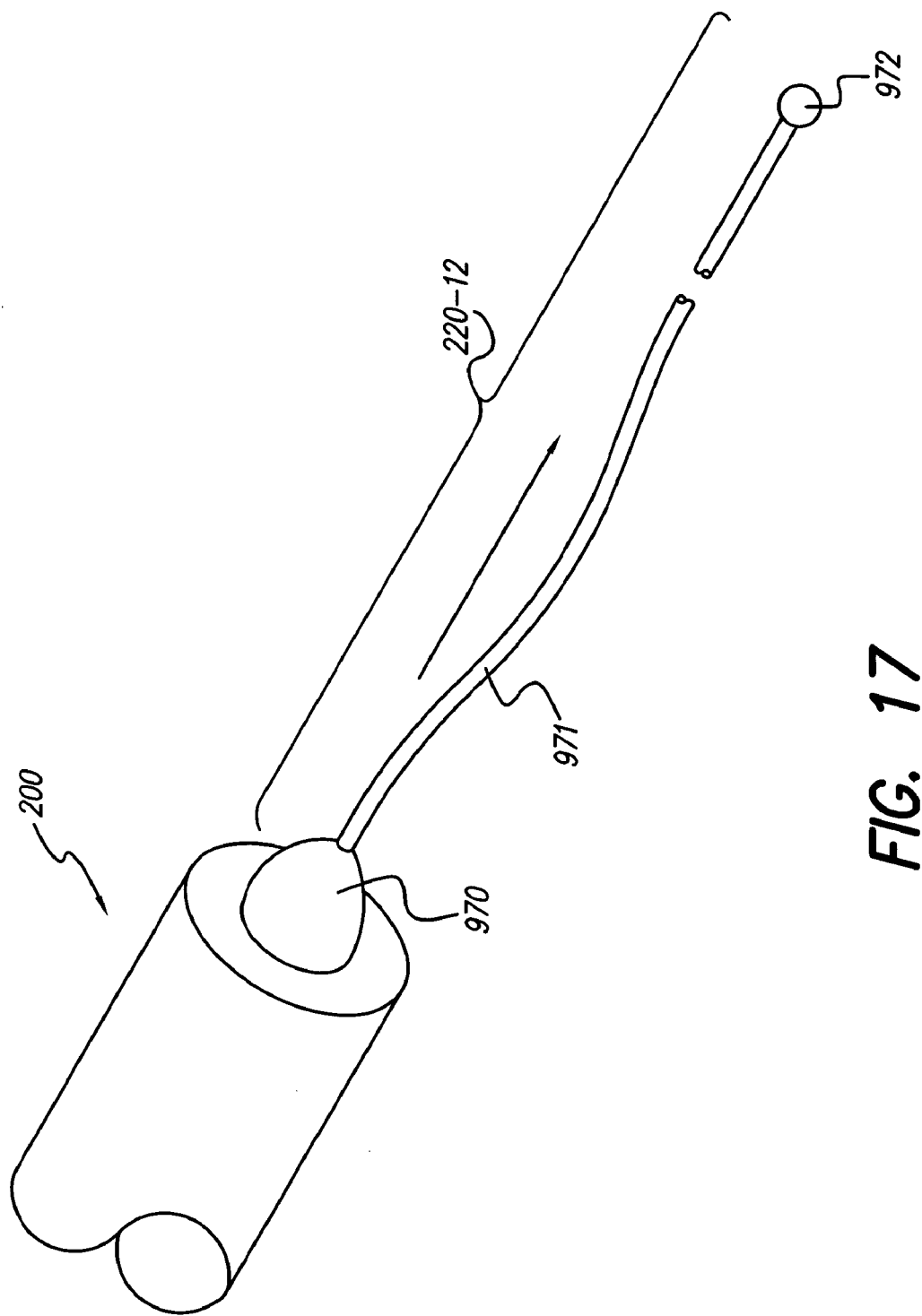
FIG. 17 is a perspective view of another exemplary engagement component according to principles described herein.

FIG. 17 is a perspective view of another exemplary engagement component (220-12) that is coupled to an implantable medical device (200). The engagement component (220-12) of FIG. 17 includes the elongated structure (960) and the engaging ring (961) described in connection with FIG. 16. The engagement component (220-12) also includes a conical member (970) coupled to the end of the implantable medical device (200). The conical member (970) is configured to dissect tissue as the medical device (200) is explanted with a force applied along the arrow illustrated in FIG. 17.

Figure 18:
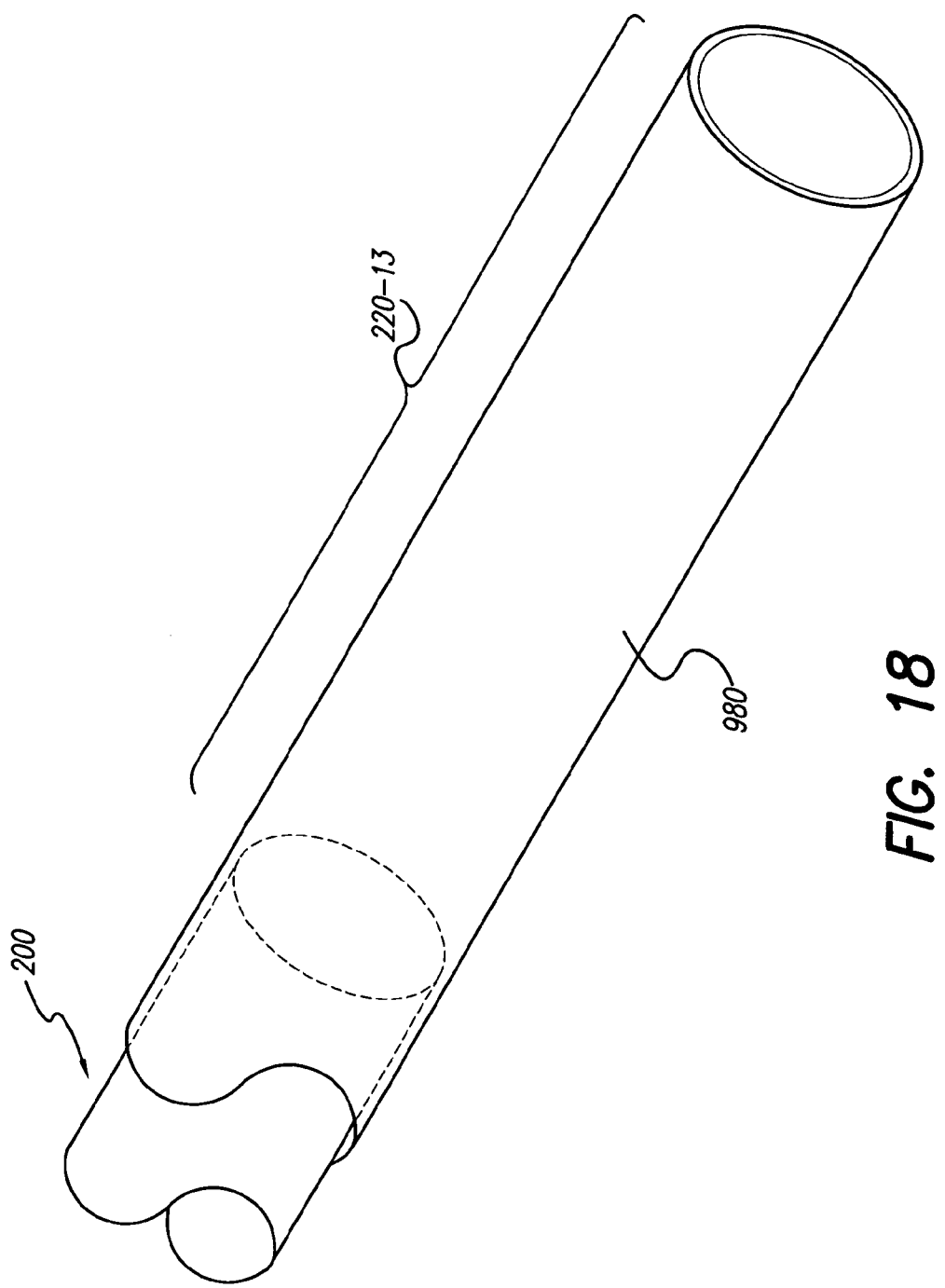
FIG. 18 is a perspective view of another exemplary engagement component according to principles described herein.

FIG. 18 is a perspective view of another exemplary engagement component (220-13) that is coupled to an implantable medical device (200). The engagement component (220-13) includes a thin, flexible tube (980) configured to engage with a number of different engagement tools as described herein or any other engagement tool specifically adapted to correspond to the engagement component (220-13). The tube (980) may also serve to permanently or temporarily house additional engagement components (220) or other structures.

Many other configurations may be used as an engagement component (220). For example, the implantable medical device (200) may include a cavity with a bar across the entry into the cavity. The bar may be used to couple the implantable medical device (200) to an engagement tool (210). The implantable medical device (200) may alternatively include a magnet that is coupled to one of its ends that may be used to magnetically couple the device (200) to an engagement tool (210) also having a magnet. Thus, the engagement components (220) described in connection with FIGS. 10-18 are merely illustrative of the many different structures that may be used to couple to an engagement tool (210) as described herein or any other engagement tool specifically adapted to correspond to the engagement components (220).

A number of exemplary methods of extracting an implanted medical device (200) will now be described. The methods described herein are merely illustrative and may be modified as best serves a particular application. It will be recognized that the methods of extracting an implanted medical device (200) described herein may be modified and used to manipulate, move, reposition, or interconnect an implanted medical device (200).

Figure 19:
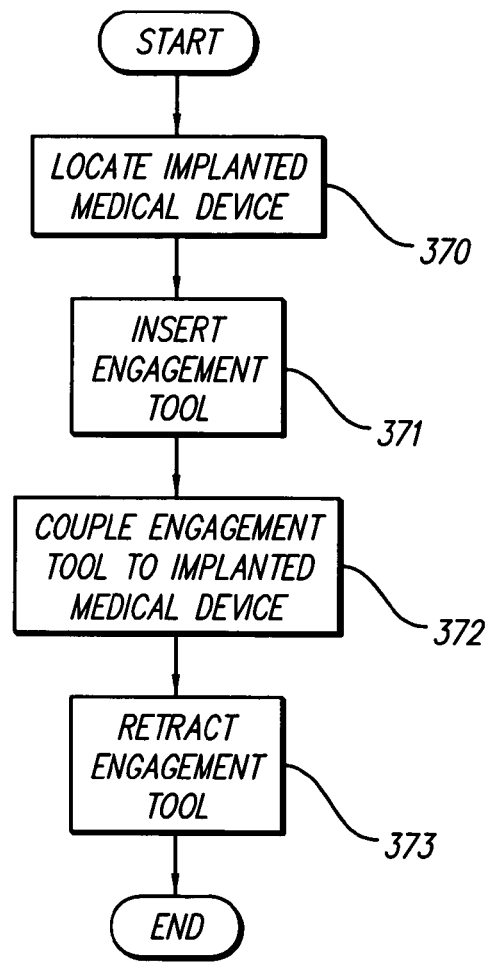
FIG. 19 is a flow chart illustrating an exemplary method of explanting an implanted medical device according to principles described herein.

FIG. 19 is a flow chart illustrating a first exemplary method of extracting an implanted medical device. The steps shown in FIG. 19 and listed below may be modified, reordered, and/or added to as best serves a particular application.

1. The implanted medical device (200) is first located (step 370). Any of a number of devices may be used in locating the implanted device (200). For example, a blunt optical needle (100; FIG. 1), live or still images from fluoroscopy, x-ray, ultrasound, computerized axial tomography (CT), positron emission tomography (PET), magnetic resonance imaging (MRI), or any other imaging device may be used to locate the implanted medical device. Manual palpation may also be used to locate the implanted medical device.

2. Once the implanted medical device (200) is located (step 370), an engagement tool (210) is inserted within the patient and advanced towards the implanted medical device (200) (step 371). The engagement tool (210) may be any of the engagement tools (210) described herein. The engagement tool (210) may be inserted through a cannula that is inserted first or may be inserted without a cannula as best serves a particular application and engagement tool configuration.

3. The engagement tool (210) is then coupled to the implanted medical device (200) (step 372). In some embodiments, the implanted medical device (200) includes an engagement component (220) configured to couple to the engagement tool (210). Alternatively, the engagement tool (210) couples directly to the implanted medical device (200).

4. Once the engagement tool (210) is coupled to the implanted medical device (step 372), the engagement tool (210) is retracted to remove the implanted medical device (200) (step 373).

One exemplary method of extracting an implanted medical device (200) includes gradually dilating a channel that leads to the implanted medical device (200). By gradually dilating the channel, the amount of tissue that is dissected is minimized, thereby reducing pain and recovery time to the patient. The method may be carried out according to the following sequence of procedures. The steps listed below may be modified, reordered, and/or added to as best serves a particular application.

1. As shown in FIG. 20A, a dissecting trocar (185) and an initial cannula (186) are inserted into a patient (190). The dissecting trocar (185) is configured to dissect tissue along a narrow path of entry into the patient. FIG. 20B shows the initial cannula (186) in more detail. As shown in FIG. 20B, the initial cannula (186) includes one or more holes (189). The purpose for these holes (186) will be described in more detail below.

2. As shown in FIG. 20C, the dissecting trocar (185) is then removed from the initial cannula (186). The initial cannula (186) is left inserted within the patient (190).

Figure 20D:
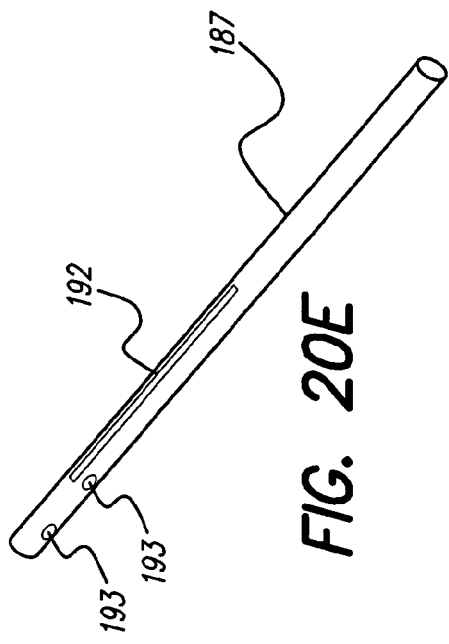
Figure 20E:
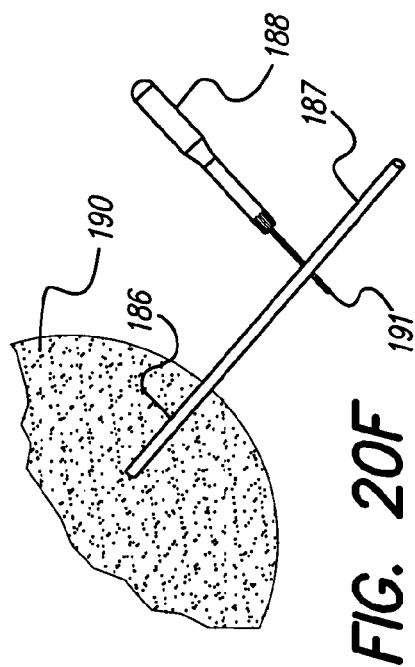

3. As shown in FIG. 20D, a second cannula (187) with a slightly larger inner diameter than the outer diameter of the initial cannula (186) is slid over the initial cannula (186) and inserted into the patient (190). The insertion of the second cannula (187) dilates the channel within the patient (190) that was created by the initial cannula (186) and trocar (185). FIG. 20E shows the second cannula (187) in more detail. As shown in FIG. 20E, the second cannula (187) may include one or more holes (193) and/or one or more slots (192). The purpose of these holes (193) and slots (192) will be described below in connection with FIG. 20F.

Figure 20F:
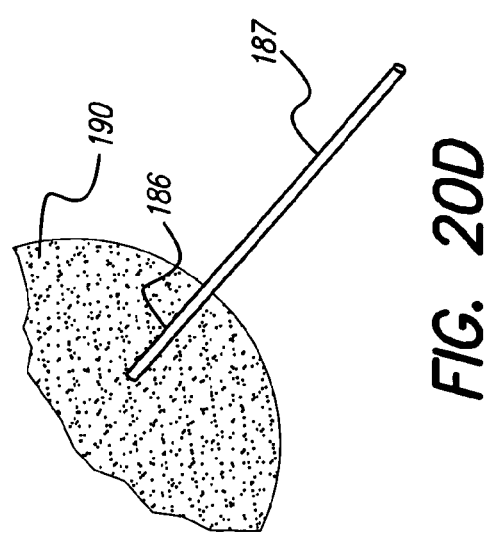
Figure 20G:
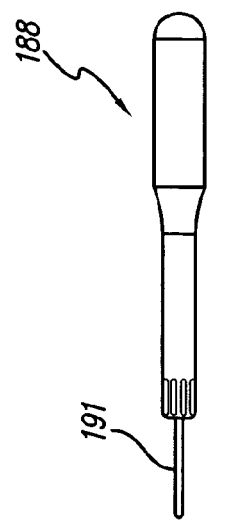

4. FIG. 20F shows that a cannula positioning tool (188) may be used to maintain the position of the initial cannula (186) while allowing the second cannula (187) to slide until the distal ends of both cannulae (186, 187) are aligned. An exemplary cannula positioning tool (188) is illustrated in FIG. 20G. In some embodiments, the tip (191) of the cannula positioning tool (188) is inserted into one of the holes (189; FIG. 20B) of the initial cannula (186) and into one of the slots (192; FIG. 20E) of the second cannula (187). The second cannula (187) is slid over the initial cannula (186) until the end of the slot (192; FIG. 20E) comes into contact with the cannula positioning tool (188) and prevents the second cannula (187) from being inserted any deeper into the patient (190). In this manner, the cannula positioning tool (188) is used to align the distal ends of both cannulae (186, 187) within the patient (190).

5. Steps 3 and 4 may be repeated with successively larger diameter cannulas until the tissue has been dilated to create a channel of sufficient diameter to explant the implanted medical device (200). Each cannula that is introduced may include the holes (193) and the slots (192) described in connection with FIG. 20E so that the distal ends of the cannulae may be aligned within the patient (190).

6. Once the channel has been sufficiently dilated, an engagement tool (210), cannula, endoscope, cyctoscope, or any other device may be inserted through the channel to engage and extract the implanted medical device (200).

It will be recognized that other techniques may be used to dilate the channel. For example, a hollow needle (e.g., a foramen needle) may be inserted within the patient to a location relatively close to the implanted medical device (200). A stiff guide wire is advanced through the needle and the needle is removed. A balloon surrounded by a sheath is inserted over the guide wire and advanced towards the implanted medical device (200). The balloon may then gradually be inflated to dilate the channel. In some embodiments, the sheath is replaced with a series of successively larger sheaths as the balloon is inflated until a sufficiently large channel is formed. The balloon and guide wire may then be removed from the channel. An engagement tool (210) is then inserted into the channel and advanced towards the implanted medical device (200). The engagement tool (210) is then used to engage and extract the implanted medical device (200).

Figure 21:
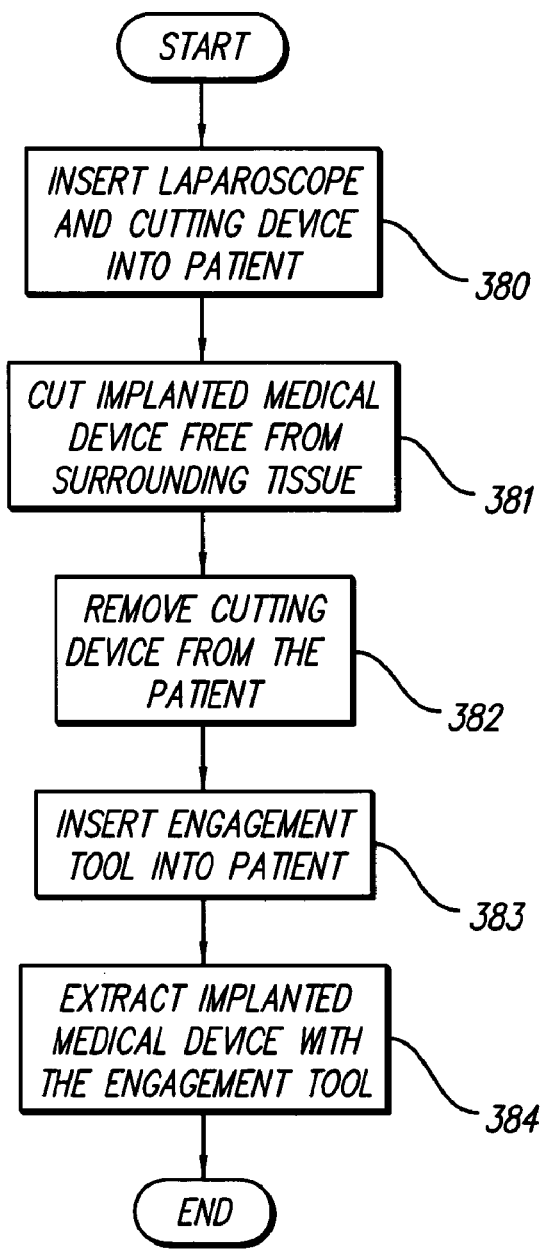
FIG. 21 is a flow chart illustrating another exemplary method of explanting an implanted medical device according to principles described herein.

FIG. 21 is a flow chart illustrating another exemplary method of extracting an implanted medical device (200). The method described in connection with FIG. 21 includes inserting a laparoscope into the patient so that the surgeon may extract the implanted medical device (200) under direct visualization. The exemplary method may be carried out according to the following sequence of procedures. The steps listed below may be modified, reordered, and/or added to as best serves a particular application.

1. A laparoscope and cutting device are inserted into the patient and advanced towards the implanted medical device (200) via the same or multiple channels using some means of visualization or by palpation (step 380).

2. The cutting device is used cut the implanted medical device (200) free from surrounding tissue (step 381). The cutting device may be a cutting wire, scissors, an electrocautery device, or any other cutting instrument. The cutting device may be a stand-alone device or it may be integrated into an engagement tool (210). An exemplary stand-alone cutting device is an optical trocar.

Figure 22A:
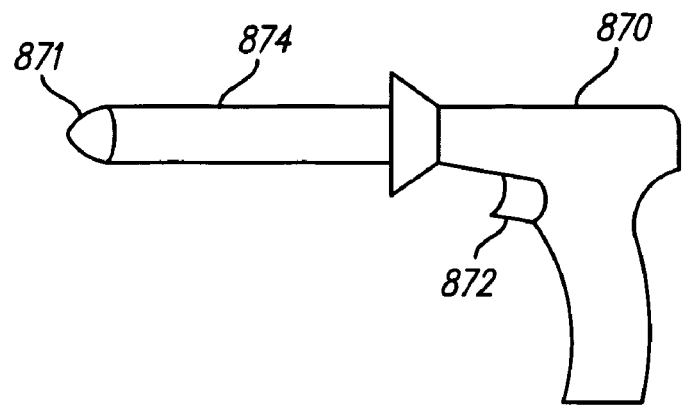
FIG. 22A is a side view of an exemplary optical trocar according to principles described herein.

FIG. 22A is a side view of an exemplary optical trocar (870). As shown in FIG. 22A, the optical trocar (870) includes an insertion member (874) that is adapted to be inserted into a patient and a cutting wire (871) disposed on a distal end of the insertion member (874). Once the insertion member (874) has been inserted into the patient, the cutting wire (871) may be used to cut the implanted medical device (200) free from surrounding tissue. In some embodiments, the cutting wire (871) is controlled with a trigger (872). For example, the depression of the trigger (872) may cause the cutting wire (871) to rotate about a central axis or otherwise move.

Figure 22B:
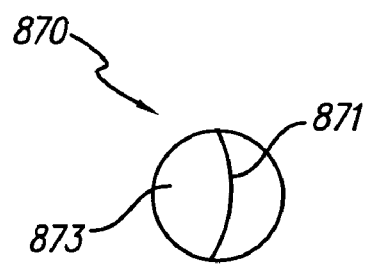
FIG. 22B is an end view of the optical trocar according to principles described herein.

FIG. 22B is an end view of the optical trocar (870) showing the cutting wire (871). The optical trocar (870) may also include a transparent window (873). The transparent window (873) is adapted to allow a surgeon to operate the optical trocar (870) under direct visualization.

Figure 22C:
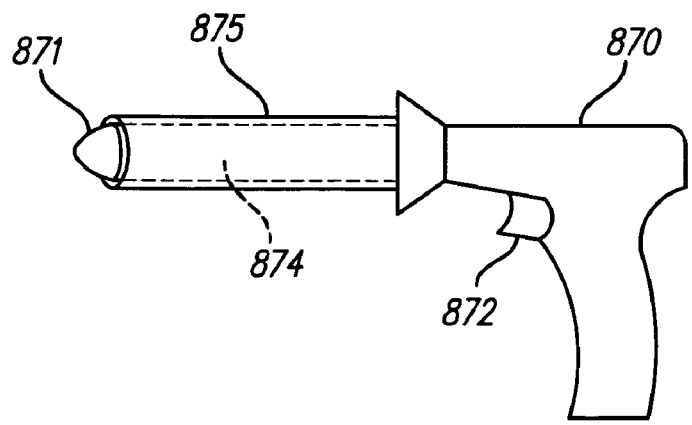
FIG. 22C is a side view of a trocar sleeve that may be placed over the insertion member of the optical trocar according to principles described herein.

FIG. 22C shows a trocar sleeve (875) that may be placed over the insertion member (874). The trocar sleeve (875) may include a channel through which air or any other suitable substance may be applied to the implanted device (200) as the cutting wire (871; FIG. 22A) frees the device (200) from surrounding tissue. The applied substance may be configured to facilitate the removal of the implanted device (200) from the surrounding tissue.

3. Returning to the flow chart of FIG. 21, once the implanted medical device (200) has been located and cut free from surrounding tissue, the cutting device may be removed from the patient (step 382).

4. An engagement tool (210) is then inserted into the patient (step 383). The engagement tool (210) may be inserted through the same channel as the laparoscope or through some other channel. It will be noted that if the cutting device is a part of an engagement tool (210), steps 3 and 4 may not be necessary because the engagement tool (210) may already be inserted within the patient.

5. With the aid of the visualization provided by the laparoscope, the engagement tool (210) is used to extract the implanted medical device (200) (step 384).

Figure 23:
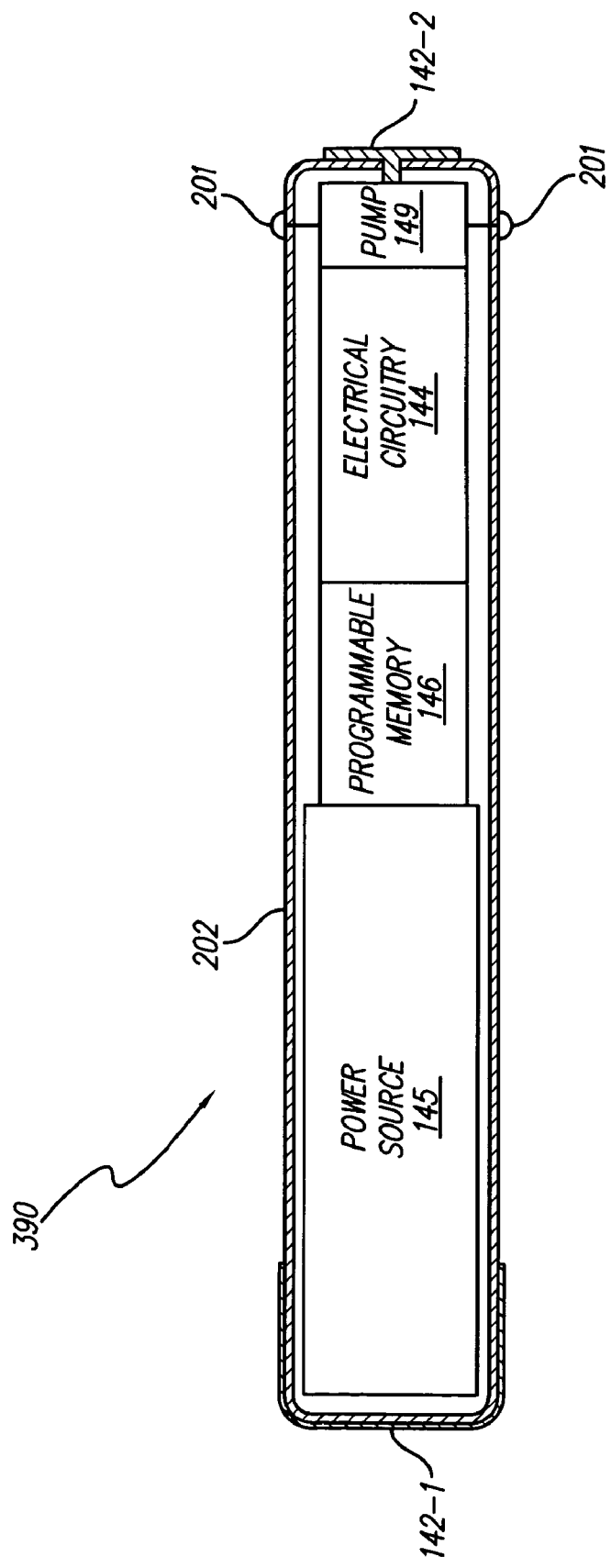
FIG. 23 illustrates an exemplary implantable stimulator according to principles described herein.

By way of example, an exemplary implantable medical device (200) will be described in connection with FIG. 23. FIG. 23 illustrates an exemplary implantable stimulator (390). This example, however, is merely illustrative of the many different implantable medical devices that may be used in connection with the engagement tools and engagement components described herein and should not be considered as limiting in any way.

As shown in FIG. 23, the stimulator (390) may include a power source (145), a programmable memory (146), electrical circuitry (144), and a coil (147). These components are housed within a capsule (202). The capsule (202) may be a thin, elongated cylinder or any other shape as best serves a particular application. In some examples, the capsule (202) may have a generally cylindrical shape with one or more flattened sides along which electrodes may be disposed. The shape of the capsule (202) may be determined by the structure of the desired target tissue, the surrounding area, the method of implantation, the size and location of the power source (145) and/or the number and arrangement of external electrodes (142). In some embodiments, the capsule (202) is substantially equal to or less than three cubic centimeters.

The power source (145) is configured to output a voltage used to supply the various components within the stimulator (390) with power. The power source (145) also provides power for any stimulation current applied with the stimulator (390) to nearby tissue. The power source (145) may be a primary battery, a rechargeable battery, a capacitor, or any other suitable power source.

The coil (148) is configured to receive and/or emit a magnetic field (also referred to as a radio frequency (RF) field) that is used to communicate with or receive power from one or more external devices that support the implanted stimulator (390), examples of which will be described below. Such communication and/or power transfer may include, but is not limited to, transcutaneously receiving data from the external device, transmitting data to the external device, and/or receiving power used to recharge the power source (145).

The programmable memory unit (146) is used for storing one or more sets of data, for example, stimulation parameters. The stimulation parameters may include, but are not limited to, electrical stimulation parameters and drug stimulation parameters. The programmable memory (146) allows a patient, clinician, or other user of the stimulator (390) to adjust the stimulation parameters such that the electrical stimulation and/or drug stimulation are at levels that are safe and efficacious for a particular medical condition and/or for a particular patient. Electrical stimulation and drug stimulation parameters may be controlled independently. However, in some instances, the electrical stimulation and drug stimulation parameters are coupled, e.g., electrical stimulation may be programmed to occur only during drug stimulation. The programmable memory (146) may be any type of memory unit such as, but not limited to, random access memory (RAM), static RAM (SRAM), a hard drive, or the like.

The electrical stimulation parameters may control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current that is applied to the target tissue. The drug stimulation parameters may control various parameters including, but not limited to, the amount of drugs infused into the target tissue, the rate of drug infusion, and the frequency of drug infusion.

Specific electrical stimulation and drug stimulation parameters may have different effects on different types of medical conditions. Thus, in some embodiments, the electrical stimulation and/or drug stimulation parameters may be adjusted by the patient, a clinician, or other user of the stimulator (390) as best serves a particular medical condition. The electrical stimulation and/or drug stimulation parameters may also be automatically adjusted by the stimulator (390), as will be described below. For example, the amplitude of the stimulus current applied to a target nerve may be adjusted to have a relatively low value to target relatively large diameter fibers of the target nerve. The stimulator (390) may also increase excitement of a target nerve by applying a stimulation current having a relatively low frequency to the target nerve (e.g., less than 100 Hz). The stimulator (390) may also decrease excitement of a target nerve by applying a relatively high frequency to the target nerve (e.g., greater than 100 Hz). The stimulator (390) may also be programmed to apply the stimulation current to a target nerve intermittently or continuously.

The stimulator (390) also includes electrodes (142-1 and 142-2) on the exterior of the capsule (200). The electrodes (142) may be disposed at either end of the capsule (202), as illustrated in FIG. 23, or placed along the length of the capsule. There may also be more than two electrodes arranged in an array. One of the electrodes (142) may be designated as a stimulating electrode to be placed close to the target tissue or treatment site and one of the electrodes (142) may be designated as an indifferent electrode used to complete a stimulation circuit.

The electrical circuitry (144) is configured to produce electrical stimulation pulses that are delivered to the target nerve via the electrodes (142). In some embodiments, the stimulator (390) may be configured to produce monopolar stimulation. The stimulator (390) may alternatively or additionally be configured to produce bipolar stimulation. Monopolar electrical stimulation is achieved, for example, using the stimulator case (202) as an indifferent electrode. Bipolar electrical stimulation is achieved, for example, using one of the electrodes of the electrode array as an indifferent electrode.

The electrical circuitry (144) may include one or more processors configured to decode stimulation parameters and generate the corresponding stimulation pulses or drug dosages. In some embodiments, the stimulator (390) has at least four channels and drives up to sixteen electrodes or more. The electrical circuitry (144) may include additional circuitry such as capacitors, integrated circuits, resistors, coils, and the like configured to perform a variety of functions as best serves a particular application.

In the example illustrated in FIG. 23, the stimulator (390) includes two or more leadless electrodes (142). However, either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the stimulator (390), while allowing most elements of the stimulator (390) to be located in a more surgically convenient site. This minimizes the distance traversed and the surgical planes crossed by the stimulator (390) and any lead(s).

The external surfaces of the stimulator (390) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The stimulator (390) may also include one or more infusion outlets (201). The infusion outlets (201) facilitate the infusion of one or more drugs into the target tissue. The infusion outlets (201) may dispense one or more drugs directly to the target tissue. Alternatively, catheters may be coupled to the infusion outlets (201) to deliver the drug therapy to target tissue some distance from the body of the stimulator (390).

If the stimulator (390) is configured to provide a drug stimulation using, for example, infusion outlets (201), the stimulator (390) may also include a pump (149) that is configured to store and dispense the one or more drugs. As indicated, the pump (149) may dispense the drug therapy through the infusion outlets (201) in the casing (202) of the stimulator (390) or may dispense drugs through catheters connected to those infusion outlets (201). In some examples, the stimulator (390) may include multiple pumps for storing and infusing dosages of the one or more drugs used to treat that particular patient's condition.

The pump or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The stimulator (390) of FIG. 23 is illustrative of many types of stimulators that may be used as the implantable medical device (200). For example, the stimulator (390) may include an implantable pulse generator (IPG) coupled to one or more leads having a number of electrodes, a spinal cord stimulator (SCS), a cochlear implant, a deep brain stimulator, a drug pump (mentioned earlier), a micro-drug pump (mentioned earlier), or any other type of implantable stimulator configured to deliver electrical and/or drug stimulation. Exemplary IPGs suitable for use as described herein include, but are not necessarily limited to, those disclosed in U.S. Pat. Nos. 6,381,496; 6,553,263; and 6,760,626. Exemplary spinal cord stimulators suitable for use as described herein include, but are not necessarily limited to, those disclosed in U.S. Pat. Nos. 5,501,703; 6,487,446; and 6,516,227. Exemplary cochlear implants suitable for use as described herein include, but are not necessarily limited to, those disclosed in U.S. Pat. Nos. 6,219,580; 6,272,382; and 6,308,101. Exemplary deep brain stimulators suitable for use as described herein include, but are not necessarily limited to, those disclosed in U.S. Pat. Nos. 5,938,688; 6,016,449; and 6,539,263. All of these listed patents are incorporated herein by reference in their respective entireties.

Alternatively, the stimulator (390) may be an implantable microstimulator, such as a BION® microstimulator (Advanced Bionics® Corporation, Valencia, Calif.). Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A medical system, comprising:
   a medical device configured to be implanted within a patient, the medical device including capsule having an exterior surface and electronic componentry sealed within the capsule; and
   an engagement tool configured to couple to the medical device post implantation, such that the engagement tool can be used to adjust the position of the medical device when coupled to the medical device and wherein the electronic componentry includes electrical circuitry configured to generate stimulation pulses or drug delivery doses in accordance with a plurality of stimulation parameters.

2. The medical system of claim 1, further comprising a cannula configured to be inserted into the patient adjacent the implanted medical device, the cannula having a lumen through which the engagement tool is configured to be inserted.

3. The medical system of claim 1, further comprising a cannula configured to be inserted into the patient adjacent the implanted medical device, the cannula having a cutting edge configured for cutting away tissue surrounding the implanted medical device to release the medical device from the tissue, the cannula further having a lumen configured for receiving the released medical device.

4. The medical system of claim 3, wherein the engagement tool includes the cannula.

5. The medical system of claim 3, wherein the engagement tool is configured to be inserted into the lumen of the cannula.

6. The medical system of claim 1, wherein a rotation of the engagement tool is configured to release the medical device from surrounding tissue.

7. The medical system of claim 1, wherein the medical device includes an engagement component affixed to the exterior surface of the medical device capsule, and wherein the engagement tool is configured to couple to the engagement component, such that the engagement tool can be used to adjust the position of the medical device when coupled to the engagement component.

8. The medical system of claim 7, wherein the engagement component includes a plurality of crenulations located about the perimeter of the engagement component, and wherein the engagement tool includes a number of teeth configured to engage the crenulations.

9. The medical system of claim 8, wherein the engagement component includes a tapered edge configured to deflect the teeth outward as the engagement tool begins to engage the engagement component, such that the teeth lock into the respective crenulations as the teeth are slid over the crenulations.

10. The medical system of claim 9, wherein each of the teeth includes a tapered edge configured to slide against the tapered edge of the engagement component as the engagement tool begins to engage the engagement component.

11. The medical system of claim 1, wherein the engagement tool includes a net configured to be tightened around the implanted medical device.

12. The medical system of claim 11, wherein the engagement tool further includes one or more wires coupled to the net for adjusting a position of the net.

13. The medical system of claim 11, wherein the engagement tool further includes a needle for guiding the net to the implanted medical device.

14. The medical system of claim 1, wherein the engagement tool includes a syringe device configured to applying a vacuum pressure to the medical device to adjust the position of the medical device.

15. The medical system of claim 14, wherein the electronic componentry includes one or more processors.

16. The medical system of claim 1, wherein the engagement tool includes a cannula configured to be inserted into the patient adjacent the implanted medical device, the cannula having a lumen configured for receiving the medical device and one or more members inwardly extending within the lumen to prevent the medical device from advancing beyond a predetermined point within the lumen.

17. The medical system of claim 1, wherein the medical device includes one or more concave notches formed in the housing of the medical device, and wherein the engagement tool includes a cannula configured to be inserted into the patient adjacent the implanted medical device, the cannula having a lumen configured for receiving the medical device and one or more corresponding convex members configured to engage with the one or more corresponding concave notches of the medical device when the medical device is received within the lumen of the cannula.

18. The medical system of claim 1, wherein the engagement tool includes a cannula configured to be inserted into the patient adjacent the implanted medical device, the cannula having a lumen configured for receiving the medical device, wherein the lumen is at least partially filled with a fluid through which energy can be transmitted to the implanted medical device to loosen the medical device from surrounding tissue.

19. The medical system of claim 1, wherein the engagement tool includes a plurality of gripping arms configured to engage the medical device.

20. The medical system of claim 19, further comprising a cannula configured to be inserted into the patient adjacent the implanted medical device, the cannula having a lumen configured for receiving the medical device and through which the engagement tool is configured to be inserted, wherein the gripping arms are configured to be placed into an open position as they extend from the lumen of the cannula, such that the open gripping arms can be disposed around the medical device, and wherein the gripping arms are configured to be placed into a closed position as they are retracted within the lumen of the cannula, such that the closed gripping arms engage the medical device.

21. The medical system of claim 1, wherein the engagement tool includes a clamping member configured to clamp onto the medical device.

22. The medical system of claim 1, wherein the engagement tool includes an adjustable loop structure configured to couple to the medical device.

23. The medical system of claim 1, wherein the engagement tool comprises a magnet configured to magnetically couple to the medical device.

24. The medical system of claim 23, wherein the electronic componentry includes one or more processors.

25. The medical system of claim 1, wherein the electronic componentry further includes memory configured for storing the plurality of stimulation parameters.

26. The medical system of claim 1, wherein the electronic componentry further includes a power source configured for supplying the electrical circuitry with power.

27. The medical system of claim 1, wherein the electronic componentry includes one or more processors.

* * * * *